US009499513B2

(12) United States Patent
Cameron et al.

(10) Patent No.: US 9,499,513 B2
(45) Date of Patent: Nov. 22, 2016

(54) ACID GENERATORS AND PHOTORESISTS COMPRISING SAME

(71) Applicant: Rohm and Haas Electronic Materials, LLC, Marlborough, MA (US)

(72) Inventors: James F. Cameron, Cambridge, MA (US); Vipul Jain, North Grafton, MA (US); Paul J. Labeaume, Auburn, MA (US); Jin Wuk Sung, Worcester, MA (US); James W. Thackeray, Braintree, MA (US)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 0 days.

(21) Appl. No.: 14/611,768

(22) Filed: Feb. 2, 2015

(65) Prior Publication Data

US 2016/0002199 A1 Jan. 7, 2016

Related U.S. Application Data

(63) Continuation of application No. 14/027,324, filed on Sep. 16, 2013, now Pat. No. 8,945,814.

(60) Provisional application No. 61/701,625, filed on Sep. 15, 2012.

(51) Int. Cl.
| | | |
|---|---|---|
| *G03F 7/004* | (2006.01) | |
| *C07D 333/76* | (2006.01) | |
| *G03F 7/027* | (2006.01) | |
| *G03F 7/20* | (2006.01) | |
| *C07C 315/00* | (2006.01) | |
| *C07D 333/46* | (2006.01) | |
| *C08F 12/30* | (2006.01) | |
| *C08F 220/24* | (2006.01) | |
| *G03F 7/038* | (2006.01) | |
| *G03F 7/039* | (2006.01) | |
| *C07C 309/17* | (2006.01) | |
| *G03F 7/16* | (2006.01) | |
| *G03F 7/32* | (2006.01) | |

(52) U.S. Cl.
CPC ........... *C07D 333/76* (2013.01); *C07C 309/17* (2013.01); *C07C 315/00* (2013.01); *C07D 333/46* (2013.01); *C08F 12/30* (2013.01); *C08F 220/24* (2013.01); *G03F 7/004* (2013.01); *G03F 7/0045* (2013.01); *G03F 7/0046* (2013.01); *G03F 7/027* (2013.01); *G03F 7/0382* (2013.01); *G03F 7/0392* (2013.01); *G03F 7/0397* (2013.01); *G03F 7/16* (2013.01); *G03F 7/20* (2013.01); *G03F 7/2004* (2013.01); *G03F 7/2059* (2013.01); *G03F 7/32* (2013.01); *C07C 2103/86* (2013.01)

(58) Field of Classification Search
CPC .... G03F 7/0045; G03F 7/0046; G03F 7/027; G03F 7/0382; G03F 7/0392; G03F 7/0397; G03F 7/20; C07D 333/00; C07D 333/46; C07C 315/00; C08F 12/30; C08F 220/24
USPC ............ 430/270.1, 322, 325, 916, 914, 942; 526/243, 245; 549/43; 568/18
See application file for complete search history.

(56) References Cited

U.S. PATENT DOCUMENTS

| | | | |
|---|---|---|---|
| 8,278,023 B2 | 10/2012 | Ichikawa et al. | |
| 8,283,105 B2 | 10/2012 | Kakinoya et al. | |
| 8,318,403 B2 | 11/2012 | Ichikawa et al. | |
| 8,354,217 B2 | 1/2013 | Ichikawa et al. | |
| 8,507,176 B2 | 8/2013 | Thackeray et al. | |
| 2008/0311522 A1 | 12/2008 | Iwai et al. | |
| 2012/0003590 A1* | 1/2012 | Hirano .................. | G03F 7/0045 430/325 |
| 2012/0135350 A1 | 5/2012 | Kobayashi et al. | |
| 2012/0282551 A1 | 11/2012 | Matsuzawa et al. | |
| 2012/0308920 A1 | 12/2012 | Domon et al. | |
| 2013/0108964 A1 | 5/2013 | Ohsawa et al. | |
| 2013/0137038 A1 | 5/2013 | Li et al. | |
| 2013/0234813 A1 | 9/2013 | Imamura et al. | |

FOREIGN PATENT DOCUMENTS

| | | |
|---|---|---|
| JP | 2011006402 A | 1/2011 |
| JP | 2011038091 A | 2/2011 |
| JP | 2011252148 A | 12/2011 |

* cited by examiner

*Primary Examiner* — Amanda C Walke
(74) *Attorney, Agent, or Firm* — Mintz Levin Cohn Ferris Glovsky and Popeo, P.C.; Peter F. Corless

(57) ABSTRACT

Acid generator compounds are provided that are particularly useful as photoresist composition components. Preferred acid generators include cyclic sulfonium compounds that comprise a covalently linked acid-labile group.

8 Claims, No Drawings

ACID GENERATORS AND PHOTORESISTS COMPRISING SAME

CROSS-REFERENCE TO RELATED APPLICATIONS

This application is a continuation of U.S. patent application Ser. No. 14/027,324, filed Sep. 16, 2013, pending, which claims priority to U.S. Provisional Application No. 61/701,625, filed Sep. 15, 2012. The contents of the foregoing applications are incorporated herein by reference in their entirety.

1. FIELD

The present invention relates to new acid generator compounds that comprise a cyclic sulfonium salt and photoresist compositions that comprise such compounds. Preferred acid generator compounds comprise one or more covalently linked acid-labile moieties.

2. INTRODUCTION

Photoresists are photosensitive films for transfer of images to a substrate. They form negative or positive images. After coating a photoresist on a substrate, the coating is exposed through a patterned photomask to a source of activating energy such as ultraviolet light to form a latent image in the photoresist coating. The photomask has areas opaque and transparent to activating radiation that define an image desired to be transferred to the underlying substrate. A relief image is provided by development of the latent image pattern in the resist coating.

Known photoresists can provide features having resolution and dimension sufficient for many existing commercial applications. However for many other applications, the need exists for new photoresists that can provide highly resolved images of submicron dimension.

Various attempts have been made to alter the make-up of photoresist compositions to improve performance of functional properties. Among other things, a variety of photoactive compounds have been reported for use in photoresist compositions. See US 20070224540 and EP 1906241. Extreme ultraviolet (EUV) and e-beam imaging technologies also have been employed. See U.S. Pat. No. 7,459,260. EUV utilizes short wavelength radiation, typically between 1 nm to 40 nm, with 13.5 nm radiation often employed.

EUV photoresist development continues to be a challenging issue for EUV Lithography (EUVL) technology implementation. Required are development of materials that can provided highly resolved fine features, including low linewidth roughness (LWR), and sufficient sensitivity to afford wafer throughput.

SUMMARY

We have now discovered new acid generator compounds particularly useful as a photoresist composition component. Acid generator compounds of the invention comprise a cyclic sulfonium salt. In preferred aspects, acid generator compounds and photoresists of the invention are particularly useful for EUV imaging.

In one aspect, acid generators are provided that comprise a cation component selected from the group consisting of:
(i) 5-(4-(2-(1-ethylcyclopentyloxy)-2-oxoethoxy)-3,5-dimethylphenyl)-5H-dibenzo[b,d]thiophenium; and
(ii) 5-(3,5-dimethyl-4-(2-oxo-2-(2-phenylpropan-2-yloxy)ethoxy)phenyl)-5H-dibenzo[b,d]thiophenium.

In a further aspect, acid generators are provided that are selected from the group consisting of:
(i) a polymerized unit of 5-(4-(2-(1-ethylcyclopentyloxy)-2-oxoethoxy)-3,5-dimethylphenyl)-5H-dibenzo[b,d]thiophenium 1,1-difluoro-2-(methacryloyloxy)ethanesulfonate; and
(ii) a polymerized unit of 5-(3,5-dimethyl-4-(2-oxo-2-(2-phenylpropan-2-yloxy)ethoxy)phenyl)-5H-dibenzo[b,d]thiophenium 1,1-difluoro-2-(methacryloyloxy)ethanesulfonate;
(iii) 5-(4-(2-(1-ethylcyclopentyloxy)-2-oxoethoxy)-3,5-dimethylphenyl)-5H-dibenzo[b,d]thiophenium 3-hydroxyadamantane-acetoxy-1,1,2,2-tetrafluorobutane-1-sulfonate;
(iv) 5-(3,5-dimethyl-4-(2-oxo-2-(2-phenylpropan-2-yloxy)ethoxy)phenyl)-5H-dibenzo[b,d]thiophenium 3-hydroxyadamantane-acetoxy-1,1,2,2-tetrafluorobutane-1-sulfonate;
(v) 5-(4-(2-(1-ethylcyclopentyloxy)-2-oxoethoxy)-3,5-dimethylphenyl)-5H-dibenzo[b,d]thiophenium 4-((4R)-4-((8R,9S,10S,13R,14S,17R)-10,13-dimethyl-3,7,12-trioxohexadecahydro-1H-cyclopenta[a]phenanthren-17-yl)pentanoyloxy)-1,1,2,2-tetrafluorobutane-1-sulfonate; and
(vi) 5-(3,5-dimethyl-4-(2-oxo-2-(2-phenylpropan-2-yloxy)ethoxy)phenyl)-5H-dibenzo[b,d]thiophenium 4-((4R)-4-((8R,9S,10S,13R,14S,17R)-10,13-dimethyl-3,7,12-trioxohexadecahydro-1H-cyclopenta[a]phenanthren-17-yl)pentanoyloxy)-1,1,2,2-tetrafluorobutane-1-sulfonate.

In certain preferred aspects, an acid generator of the invention may be covalently linked to a polymer. Such polymer may be suitably utilized as a component of a photoresist composition. The polymer may comprise acid-labile groups in addition to the covalently linked acid generator compounds. In such aspects, suitably the anion component but not the cation component of an ionic acid generator compound of the invention may be covalently linked to a polymer, or the cation component but not the anion component of the acid generator may be covalently linked to a polymer, or each of the anion and cation components of the acid generator may be covalently linked to a polymer.

Preferred photoresists of the invention may comprise an imaging-effective amount of one or more acid generator compounds as disclosed herein and a suitable polymer component. Photoresists of the invention also may comprise a mixture of distinct acid generator compounds, typically a mixture of 2 or 3 different acid generator compounds, more typically a mixture that consists of a total of 2 distinct acid generator compounds.

Methods are also provided for forming relief images of photoresist compositions of the invention (including patterned lines with sub sub-50 nm or sub-20 nm dimensions). Substrates such as a microelectronic wafer also are provided having coated thereon a photoresist composition of the invention.

DETAILED DESCRIPTION

As referred to herein, acid generator compounds can produce an acid when exposed to activating radiation, such as EUV radiation, e-beam radiation or other radiation sources such as 193 nm wavelength radiation. Acid generator compounds as referred to herein also may be referred to as photoacid generator compounds.

Additional acid generator compounds of the invention include those comprising at least of the following cation components:
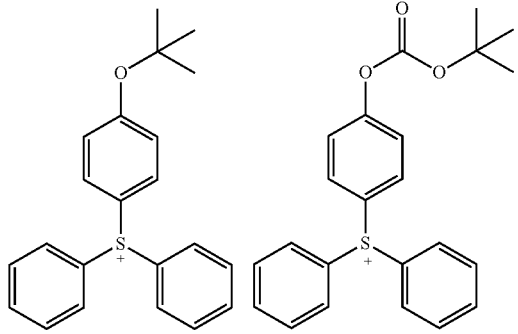
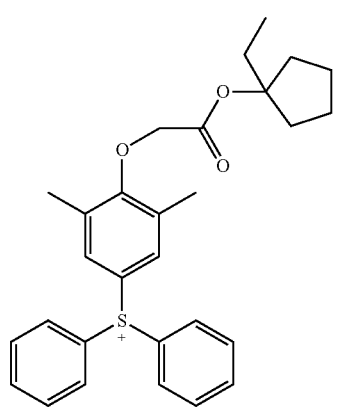
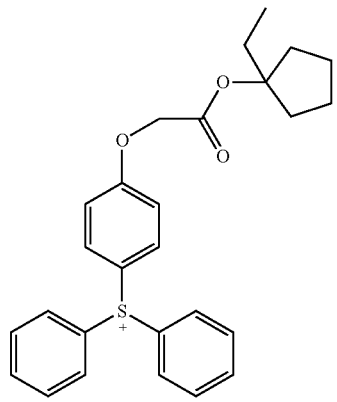
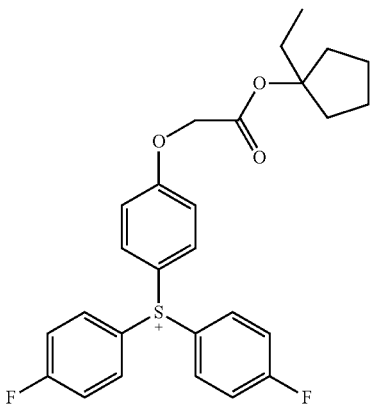
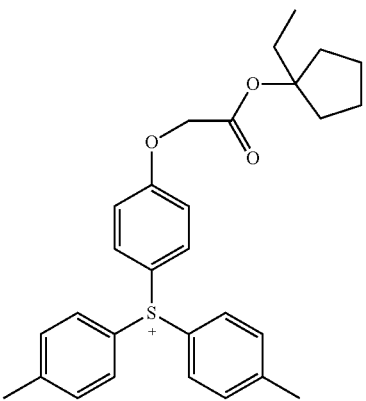
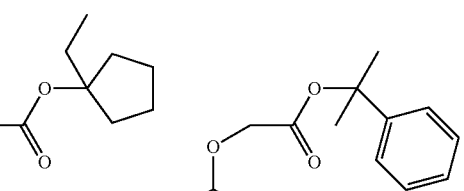
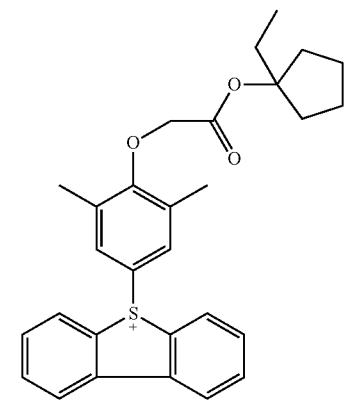
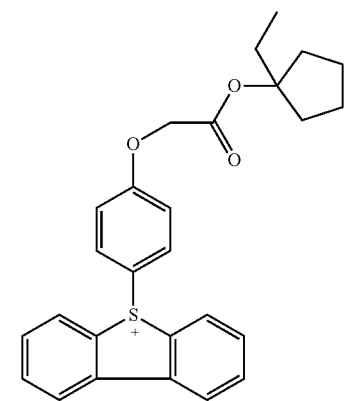

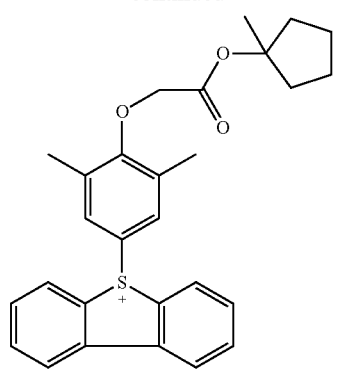
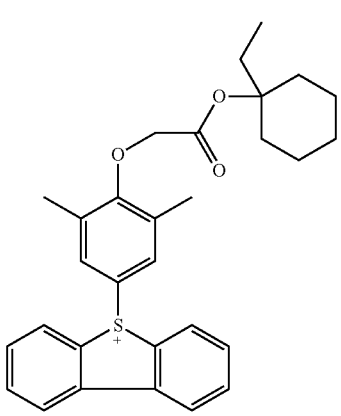
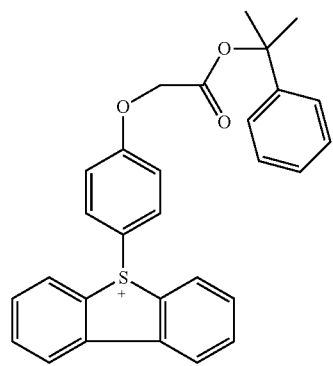
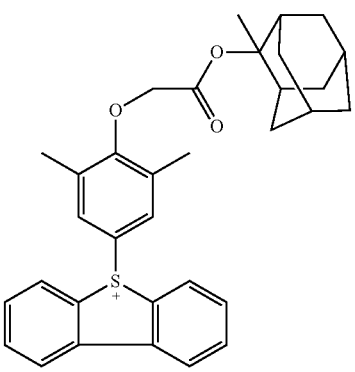
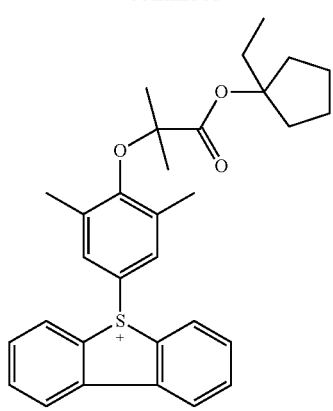
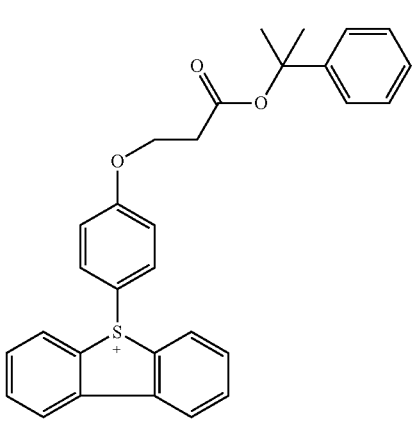
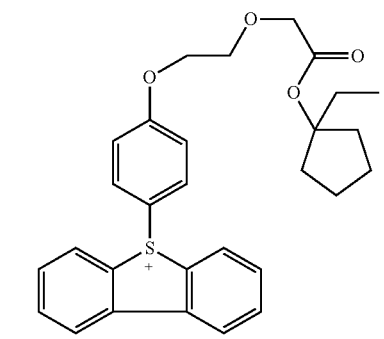
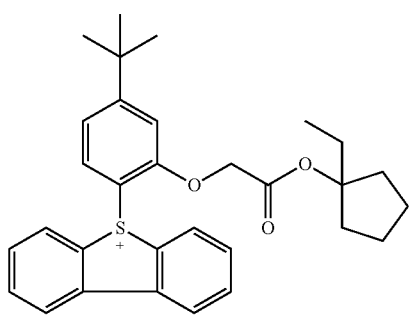

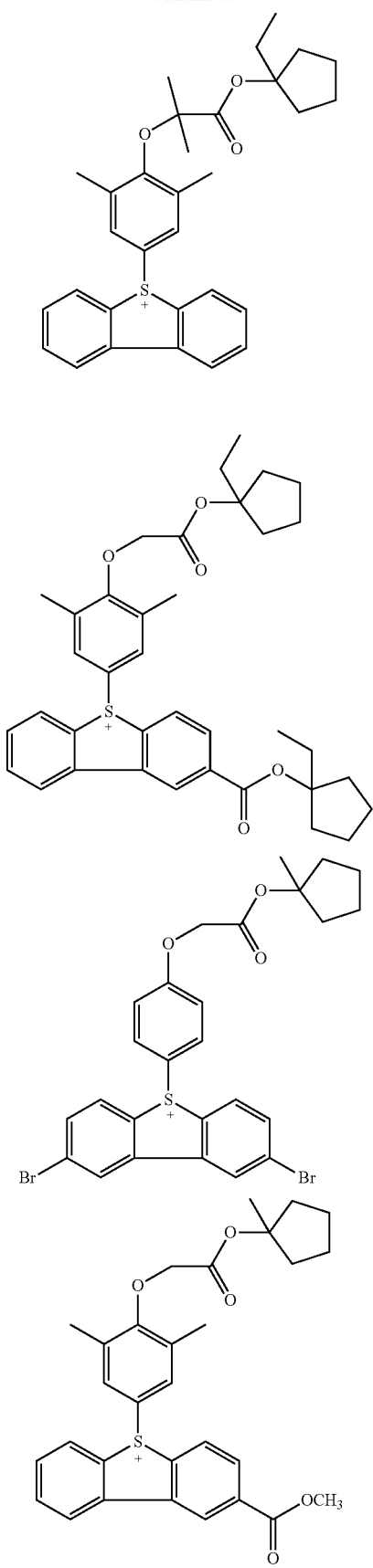
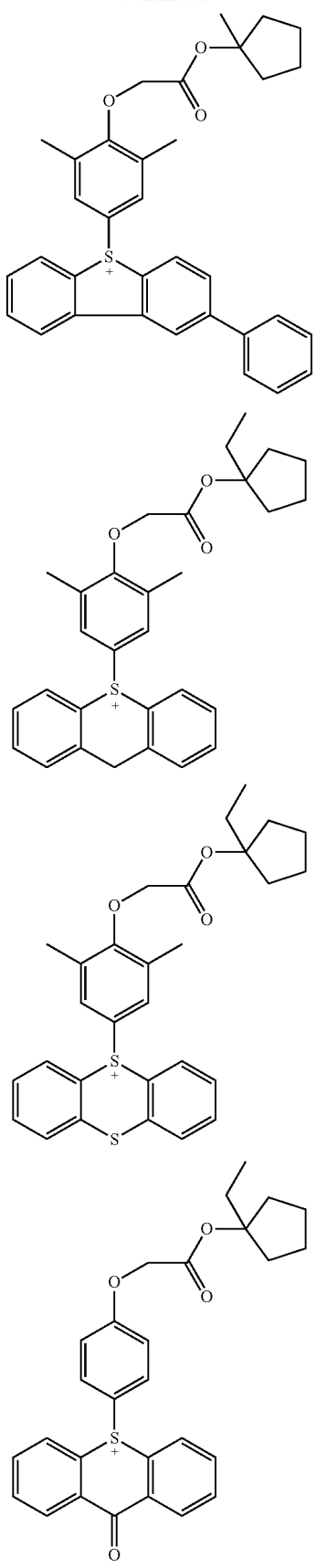

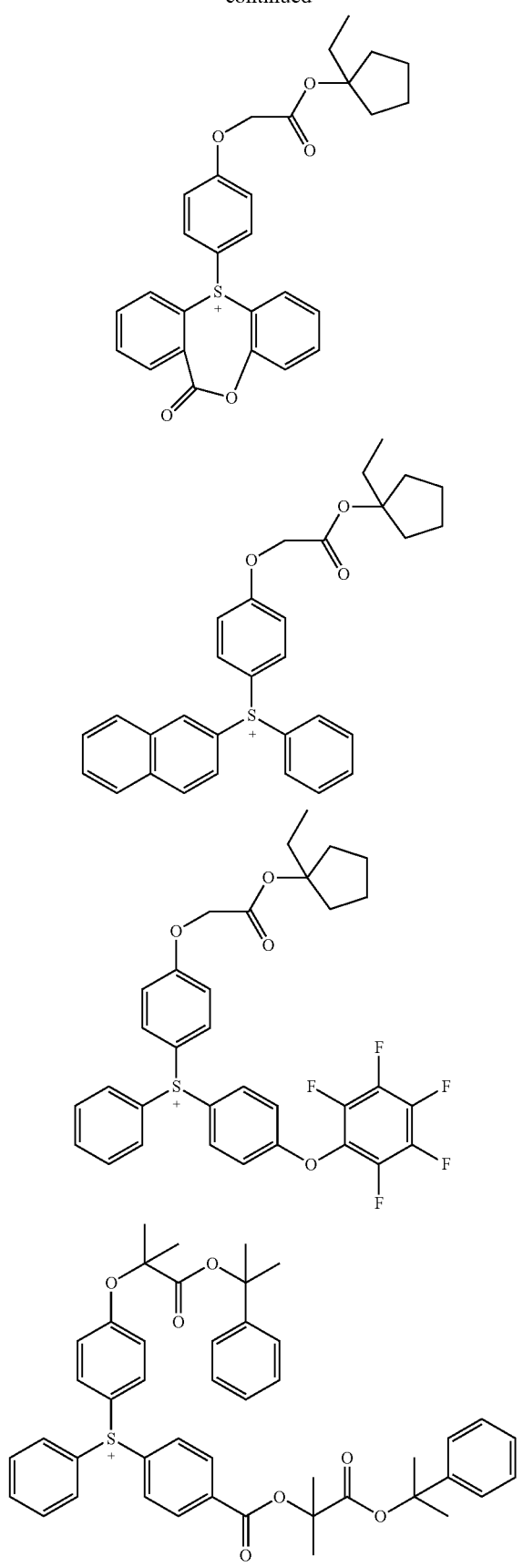
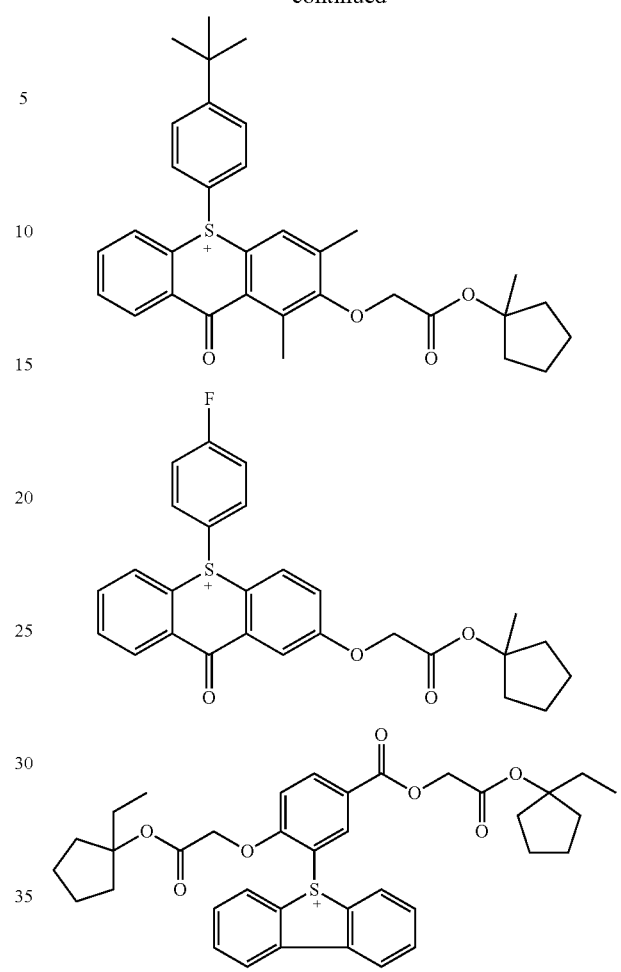
Specifically preferred anion components of acid generators of the invention include the following:
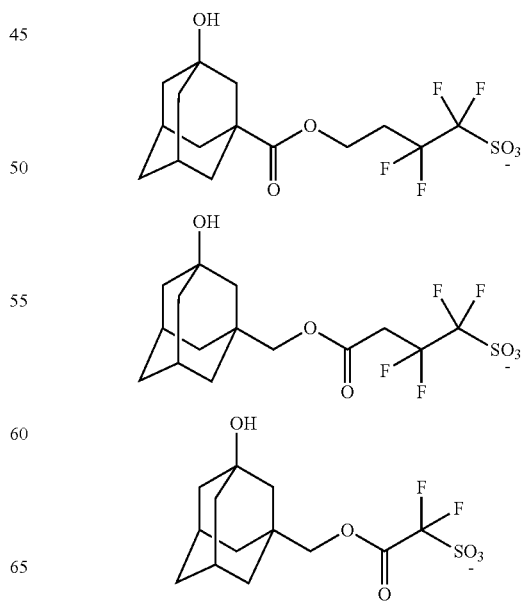

-continued

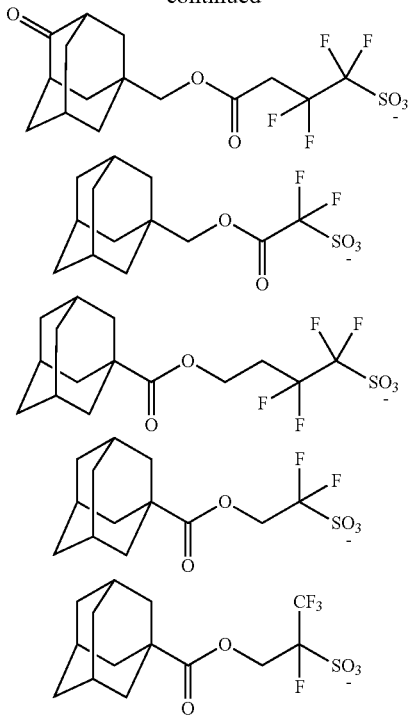

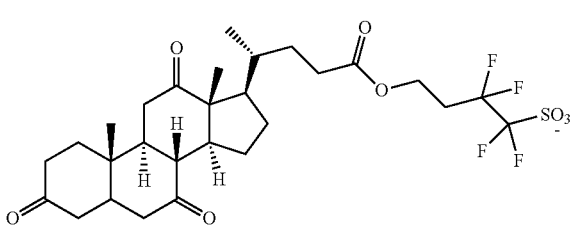

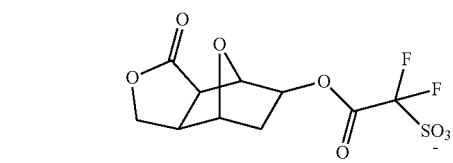

Acid generator compounds of the invention can be readily prepared. Exemplary preferred syntheses are set forth in the examples which follow. Thus, for instance, dibenzothiophene oxide can be functionalized to provide a sulfonium salt, such as by reaction with a substituted phenyl reagent suitably in the presence of Eaton's reagent. The thus formed sulfonium salt can be further functionalized as desired, such as to provide one or more covalently linked acid-labile groups.

As discussed above, acid generator compounds as disclosed herein are useful as the radiation sensitive component in photoresist compositions, including both positive-acting and negative-acting chemically amplified resist compositions.

The photoresists of the invention typically comprise a polymer and one or more acid generator compounds as disclosed herein. Preferably the polymer has functional groups that impart alkaline aqueous developability to the resist composition. For example, preferred are polymers that comprise polar functional groups such as hydroxyl or carboxylate, or acid-labile groups that can liberate such polar moieties upon lithographic processing. Preferably the polymer is used in a resist composition in an amount sufficient to render the resist developable with an aqueous alkaline solution.

Acid generator compounds of the invention are also suitably used with polymers that comprise repeat units containing aromatic groups, such as optionally substituted phenyl including phenol, optionally substituted naphthyl, and optionally substituted anthracene. Optionally substituted phenyl (including phenol) containing polymers are particularly suitable for many resist systems, including those imaged with EUV and e-beam radiation. For positive-acting resists, the polymer also preferably contains one or more repeat units that comprise acid-labile groups. For example, in the case of polymers containing optionally substituted phenyl or other aromatic groups, a polymer may comprise repeat units that contain one or more acid-labile moieties such as a polymer that is formed by polymerization of monomers of an acrylate or methacrylate compound with acid-labile ester (e.g. t-butyl acrylate or t-butyl methacrylate). Such monomers may be copolymerized with one or more other monomers that comprise aromatic group(s) such as optionally phenyl, e.g. a styrene or vinyl phenol monomer.

Preferred monomers used for the formation of such polymers include: an acid-deprotectable monomer having the formula (V), a lactone-containing monomer of the formula (VI), a base-soluble monomer of formula (VII) for adjusting dissolution rate in alkaline developer, and a photoacid-generating monomer of the formula (VIII), or a combination comprising at least one of the foregoing monomers:

(V)

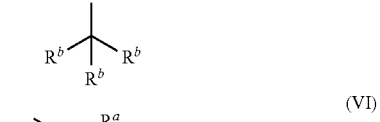

(VI)

(VII)

(VIII)

wherein each $R^a$ is independently H, F, —CN, $C_{1-10}$ alkyl, or $C_{1-10}$ fluoroalkyl. In the acid-deprotectable monomer of formula (V), $R^b$ is independently $C_{1-20}$ alkyl, $C_{3-20}$ cycloalkyl, $C_{6-20}$ aryl, or $C_{7-20}$ aralkyl, and each $R^b$ is separate or at least one $R^b$ is bonded to an adjacent $R^b$ to form a cyclic structure. In lactone-containing monomer of formula (VI), L is a monocyclic, polycyclic, or fused polycyclic $C_{4-20}$ lactone-containing group. In the base solubilizing monomer of formula (VII), W is a halogenated or non-halogenated, aromatic or non-aromatic $C_{2-50}$ hydroxyl-containing organic group having a pKa of less than or equal to 12. In the photoacid generating monomer of formula (VIII), Q is ester-containing or non-ester containing and fluorinated or non-fluorinated and is $C_{1-20}$ alkyl, $C_{3-20}$ cycloalkyl, $C_{6-20}$ aryl, or $C_{7-20}$ aralkyl group, A is ester-containing or non-ester-containing and fluorinated or non-fluorinated, and is $C_{1-20}$ alkyl, $C_{3-20}$ cycloalkyl, $C_{6-20}$ aryl, or $C_{7-20}$ aralkyl, $Z^-$ is an anionic moiety comprising carboxylate, sulfonate, an anion of a sulfonamide, or an anion of a sulfonimide, and $G^+$ is a sulfonium or iodonium cation.

Exemplary acid-deprotectable monomers include but are not limited to:

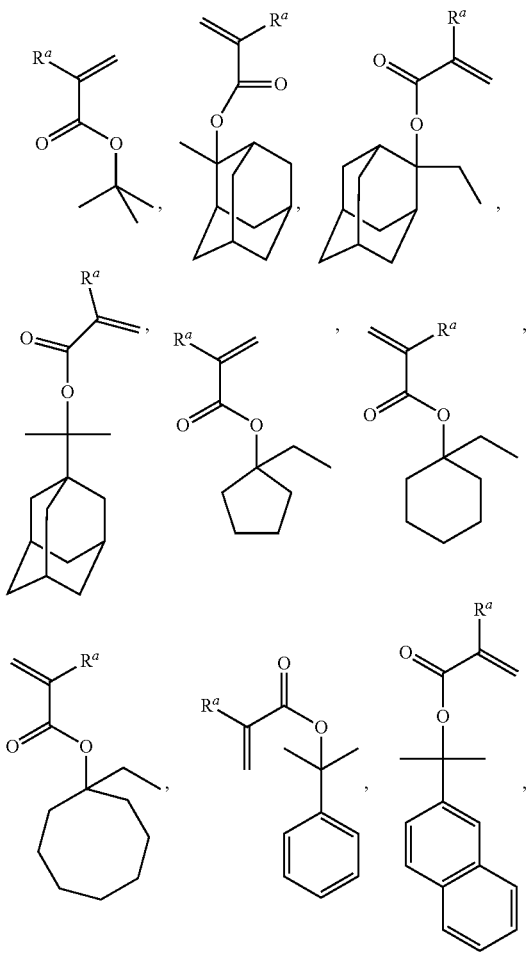

or a combination comprising at least one of the foregoing, wherein $R^a$ is H, F, —CN, $C_{1-6}$ alkyl, or $C_{1-6}$ fluoroalkyl.

Suitable lactone monomers may be of the following formula (IX):

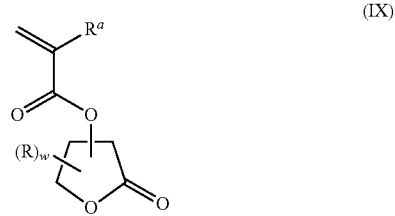

wherein $R^a$ is H, F, —CN, $C_{1-6}$ alkyl, or $C_{1-6}$ fluoroalkyl, R is a $C_{1-10}$ alkyl, cycloalkyl, or heterocycloalkyl, and w is an integer of 0 to 5. In formula (IX), R is attached directly to the lactone ring or commonly attached to the lactone ring and/or one or more R groups, and the ester moiety is attached to the lactone ring directly, or indirectly through R.

Exemplary lactone-containing monomers include:

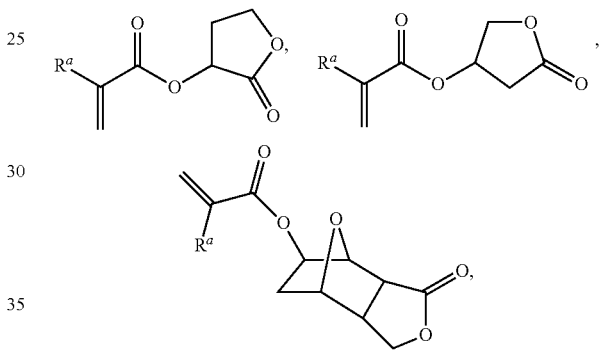

or a combination comprising at least one of the foregoing monomers, wherein $R^a$ is H, F, —CN, $C_{1-10}$ alkyl, or $C_{1-10}$ fluoroalkyl.

Suitable base-soluble monomers may be of the following formula (X):

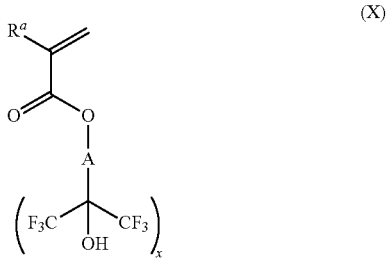

wherein each $R^a$ is independently H, F, —CN, $C_{1-10}$ alkyl, or $C_{1-10}$ fluoroalkyl, A is a hydroxyl-containing or non-hydroxyl containing, ester-containing or non ester-containing, fluorinated or non-fluorinated $C_{1-20}$ alkylene, $C_{3-20}$ cycloalkylene, $C_{6-20}$ arylene, or $C_{7-20}$ aralkylene, and x is an integer of from 0 to 4, wherein when x is 0, A is a hydroxyl-containing $C_{6-20}$ arylene.

Exemplary base soluble monomers include those having the following structures:

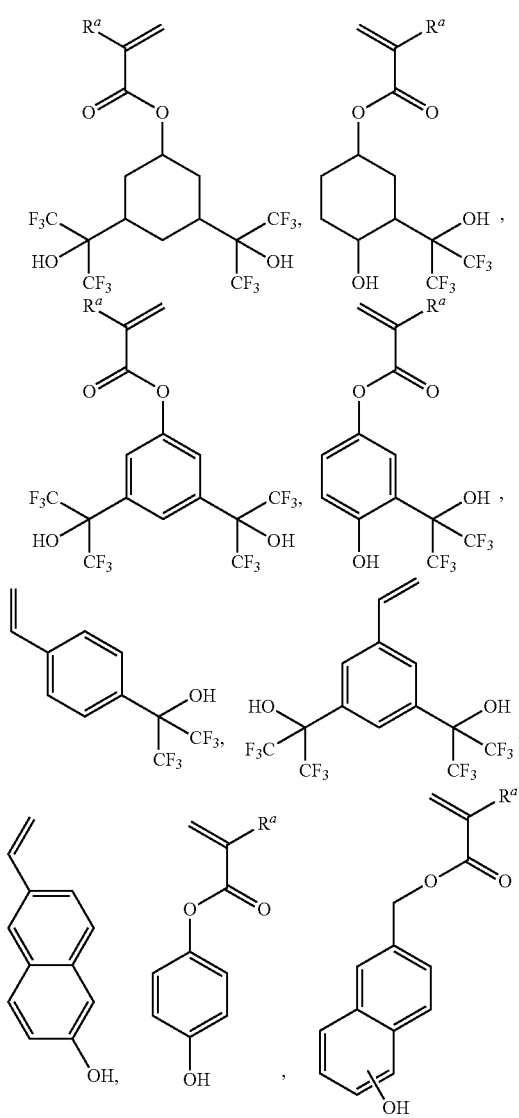

or a combination comprising at least one of the foregoing, wherein $R^a$ is H, F, —CN, $C_{1-6}$ alkyl, or $C_{1-6}$ fluoroalkyl.

Preferred photoacid generating monomer include those of the formulae (XI) or (XII):

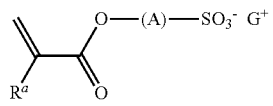
(XI)

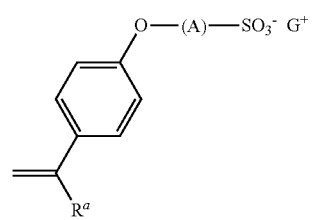
(XII)

wherein each $R^a$ is independently H, F, —CN, $C_{1-6}$ alkyl, or $C_{1-6}$ fluoroalkyl, A is a fluorine-substituted $C_{1-30}$ alkylene group, a fluorine-substituted $C_{3-30}$ cycloalkylene group, a fluorine-substituted $C_{6-30}$ arylene group, or a fluorine-substituted $C_{7-30}$ alkylene-arylene group, and $G^+$ is a sulfonium or iodonium cation.

Preferably, in formulas (XI) and (XII), A is a —[(C($R^1$)$_2$)$_x$C(=O)O]$_b$—C($R_2$)$_2$)$_y$(CF$_2$)$_z$— group, or an o-, m- or p-substituted —C$_6$F$_4$— group, where each $R^1$ and $R^2$ are each independently H, F, —CN, $C_{1-6}$ fluoroalkyl, or $C_{1-6}$ alkyl, b is 0 or 1, x is an integer of 1 to 10, y and z are independently integers of from 0 to 10, and the sum of y+z is at least 1.

Exemplary preferred photoacid generating monomers include:

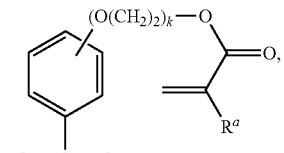

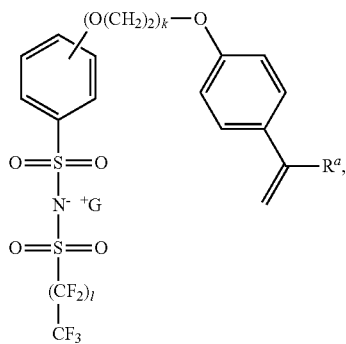

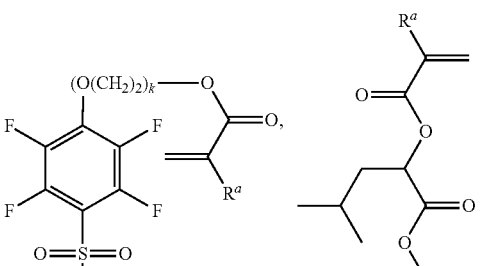

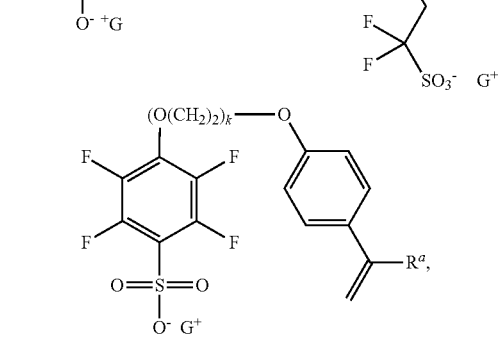

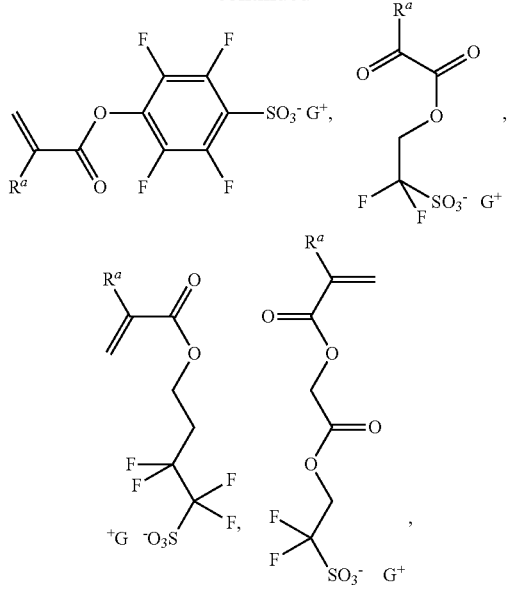

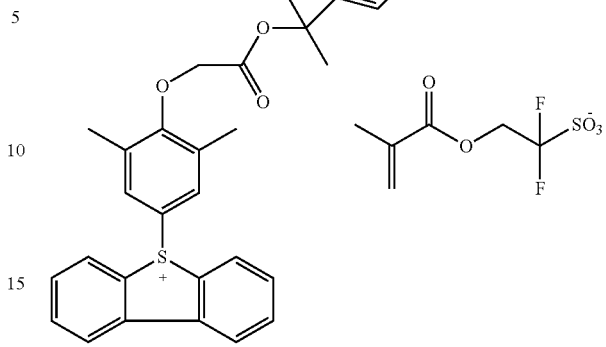

or a combination comprising at least one of the foregoing, where each $R^a$ is independently H, F, —CN, $C_{1-6}$ alkyl, or $C_{1-6}$ fluoroalkyl, k is suitably an integer of from 0 to 5; and G is a sulfonium or iodonium cation.

Preferred photoacid-generating monomers may include sulfonium or iodonium cation. Preferably, in formula (IV), $G^+$ is of the formula (XIII):

(XIII)

wherein X is S or I, each $R^0$ is halogenated or non-halogenated and is independently $C_{1-30}$ alkyl group; a polycyclic or monocyclic $C_{3-30}$ cycloalkyl group; a polycyclic or monocyclic $C_{4-30}$ aryl group; or a combination comprising at least one of the foregoing, wherein when X is S, one of the $R^0$ groups is optionally attached to one adjacent $R^0$ group by a single bond, and a is 2 or 3, wherein when X is I, a is 2, or when X is S, a is 3.

Exemplary acid generating monomers include those having the formulas:

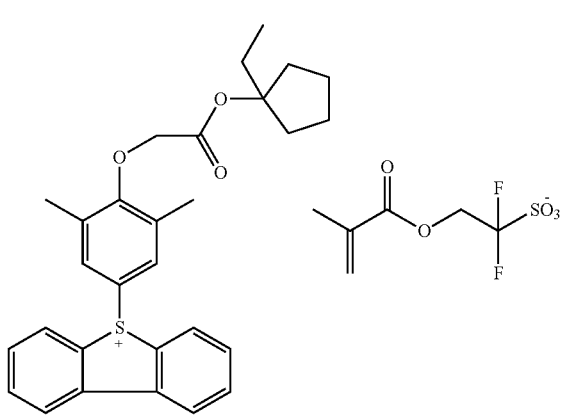

wherein $R^a$ is H, F, —CN, $C_{1-6}$ alkyl, or $C_{1-6}$ fluoroalkyl.

Specifically suitable polymers that have acid-labile deblocking groups for use in a positive-acting chemically-amplified photoresist of the invention have been disclosed in European Patent Application 0829766A2 (polymers with acetal and ketal polymers) and European Patent Application EP0783136A2 (terpolymers and other copolymers including units of 1) styrene; 2) hydroxystyrene; and 3) acid labile groups, particularly alkyl acrylate acid labile groups.

Polymers for use in photoresists of the invention may suitably vary widely in molecular weight and polydisperity. Suitable polymers include those that have a $M_w$ of from about 1,000 to about 50,000, more typically about 2,000 to about 30,000 with a molecular weight distribution of about 3 or less, more typically a molecular weight distribution of about 2 or less.

Preferred negative-acting compositions of the invention comprise a mixture of materials that will cure, crosslink or harden upon exposure to acid, and a photoactive component of the invention. Preferred negative acting compositions comprise a polymer binder such as a phenolic or non-aromatic polymer, a crosslinker component and a photoactive component of the invention. Such compositions and the use thereof have been disclosed in European Patent Applications 0164248 and U.S. Pat. No. 5,128,232 to Thackeray et al. Preferred phenolic polymers for use as the polymer binder component include novolaks and poly(vinylphenol)s such as those discussed above. Preferred crosslinkers include amine-based materials, including melamine, glycolurils, benzoguanamine-based materials and urea-based materials. Melamine-formaldehyde polymers are often particularly suitable. Such crosslinkers are commercially available, e.g. the melamine polymers, glycoluril polymers, urea-based polymer and benzoguanamine polymers, such as those sold by Cytec under tradenames Cymel 301, 303, 1170, 1171, 1172, 1123 and 1125 and Beetle 60, 65 and 80.

Photoresists of the invention also may contain other materials. For example, other optional additives include actinic and contrast dyes, anti-striation agents, plasticizers, speed enhancers, sensitizers, photodestroyable bases etc. Such optional additives typically will be present in minor concentration in a photoresist composition.

Inclusion of base materials, preferably the carboxylate or sulfonate salts of photo-decomposable cations, provides a mechanism for neutralization of acid from the acid decomposable groups, and limits the diffusion of the photogenerated acid, to thereby provide improved contrast in the photoresist.

Photo-destroyable bases include photo-decomposable cations, and preferably those also useful for preparing acid generator compounds, paired with an anion of a weak (pKa>2) acid such as, for example, a $C_{1-20}$ carboxylic acid.

Exemplary such carboxylic acids include formic acid, acetic acid, propionic acid, tartaric acid, succinic acid, cyclohexylcarboxylic acid, benzoic acid, salicylic acid, and other such carboxylic acids.

Alternatively, or in addition, other additives may include quenchers that are non-photo-destroyable bases, such as, for example, those based on hydroxides, carboxylates, amines, imines, and amides. Preferably, such quenchers include $C_{1-30}$ organic amines, imines, or amides, or may be a $C_{1-30}$ quaternary ammonium salt of a strong base (e.g., a hydroxide or alkoxide) or a weak base (e.g., a carboxylate). Exemplary quenchers include amines such as tripropylamine, dodecylamine, 1,1',1''-nitrilotripropan-2-ol, 1,1',1'',1'''-(ethane-1,2-diylbis(azanetriyl))tetrapropan-2-ol; aryl amines such as diphenylamine, triphenylamine, aminophenol, and 2-(4-aminophenyl)-2-(4-hydroxyphenyl)propane, Troger's base, a hindered amine such as diazabicycloundecene (DBU) or diazabicyclononene (DBN), or ionic quenchers including quaternary alkyl ammonium salts such as tetrabutylammonium hydroxide (TBAH) or tetrabutylammonium lactate.

Surfactants include fluorinated and non-fluorinated surfactants, and are preferably non-ionic. Exemplary fluorinated non-ionic surfactants include perfluoro $C_4$ surfactants such as FC-4430 and FC-4432 surfactants, available from 3M Corporation; and fluorodiols such as POLYFOX PF-636, PF-6320, PF-656, and PF-6520 fluorosurfactants from Omnova.

The photoresist further includes a solvent generally suitable for dissolving, dispensing, and coating the components used in a photoresists. Exemplary solvents include anisole, alcohols including ethyl lactate, 1-methoxy-2-propanol, and 1-ethoxy-2 propanol, esters including n-butylacetate, 1-methoxy-2-propyl acetate, methoxyethoxypropionate, ethoxyethoxypropionate, ketones including cyclohexanone and 2-heptanone, and a combination comprising at least one of the foregoing solvents.

Such photoresists may include the copolymer in an amount of 50 to 99 wt %, specifically 55 to 95 wt %, more specifically 60 to 90 wt %, and still more specifically 65 to 90 based on the total weight of solids. The photo-destroyable base may be present in the photoresist in an amount of 0.01 to 5 wt %, specifically 0.1 to 4 wt %, and still more specifically 0.2 to 3 wt %, based on the total weight of solids. A surfactant may be included in an amount of 0.01 to 5 wt %, specifically 0.1 to 4 wt %, and still more specifically 0.2 to 3 wt %, based on the total weight of solids. A quencher may be included in relatively small amounts of for example, from 0.03 to 5 wt % based on the total weight of solids. Other additives may be included in amounts of less than or equal to 30 wt %, specifically less than or equal to 20%, or more specifically less than or equal to 10%, based on the total weight of solids. The total solids content for the photoresist composition may be 0.5 to 50 wt %, specifically 1 to 45 wt %, more specifically 2 to 40 wt %, and still more specifically 5 to 30 wt %, based on the total weight of solids and solvent. The acid generator compound(s) should be present in an amount sufficient to enable generation of a latent image in a coating layer of the resist. More specifically, the one or more acid generator compounds will suitably be present in an amount of from about 1 to 50 weight percent of total solids of a resist. It will be understood that the solids includes copolymer, photo-destroyable base, quencher, surfactant, any added PAG, and any optional additives, exclusive of solvent.

A coated substrate may be formed from the photoresist containing acid generator compound(s) which should be present in an amount sufficient to enable generation of a latent image in a coating layer of the resist and acid generator compound. Such a coated substrate includes: (a) a substrate having one or more layers to be patterned on a surface thereof; and (b) a layer of the photoresist composition including the acid generator compound over the one or more layers to be patterned. For EUV or e beam imaging, photoresists may suitably have relatively higher content of acid generator compound(s), e.g. where the one or more acid generator compounds comprise 5 to 10 to about 65 weight percent of total solids of the resist. Typically, lesser amounts of the photoactive component will be suitable for chemically amplified resists.

The photoresists of the invention are generally prepared following known procedures with the exception that one or more acid generator compounds of the invention are substituted for prior photoactive compounds used in the formulation of such photoresists. The photoresists of the invention can be used in accordance with known procedures.

Substrates may be any dimension and shape, and are preferably those useful for photolithography, such as silicon, silicon dioxide, silicon-on-insulator (SOI), strained silicon, gallium arsenide, coated substrates including those coated with silicon nitride, silicon oxynitride, titanium nitride, tantalum nitride, ultrathin gate oxides such as hafnium oxide, metal or metal coated substrates including those coated with titanium, tantalum, copper, aluminum, tungsten, alloys thereof, and combinations thereof. Preferably, the surfaces of substrates herein include critical dimension layers to be patterned including, for example, one or more gate-level layers or other critical dimension layer on the substrates for semiconductor manufacture. Such substrates may preferably include silicon, SOI, strained silicon, and other such substrate materials, formed as circular wafers having dimensions such as, for example, 20 cm, 30 cm, or larger in diameter, or other dimensions useful for wafer fabrication production.

Further, a method of forming an electronic device includes (a) applying a layer of a photoresist composition including on a surface of the substrate; (b) patternwise exposing the photoresist composition layer to activating radiation; and (c) developing the exposed photoresist composition layer to provide a resist relief image.

Applying may be accomplished by any suitable method, including spin coating, spray coating, dip coating, doctor blading, or the like. Applying the layer of photoresist is preferably accomplished by spin-coating the photoresist in solvent using a coating track, in which the photoresist is dispensed on a spinning wafer. During dispense, the wafer may be spun at a speed of up to 4,000 rpm, preferably from about 500 to 3,000 rpm, and more preferably 1,000 to 2,500 rpm. The coated wafer is spun to remove solvent, and baked on a hot plate to remove residual solvent and free volume from the film to make it uniformly dense.

Patternwise exposure is then carried out using an exposure tool such as a stepper, in which the film is irradiated through a pattern mask and thereby is exposed pattern-wise. The method preferably uses advanced exposure tools generating activating radiation at wavelengths capable of high resolution including extreme-ultraviolet (EUV) or e-beam radiation. It will be appreciated that exposure using the activating radiation decomposes the PAG in the exposed areas and generates acid and decomposition by-products, and that the acid then effects a chemical change in the polymer (deblocking the acid sensitive group to generate a base-soluble group, or alternatively, catalyzing a cross-linking reaction in the exposed areas). The resolution of such exposure tools may be less than 30 nm.

Developing the exposed photoresist layer is then accomplished by treating the exposed layer to a suitable developer capable of selectively removing the exposed portions of the film (where the photoresist is positive tone) or removing the unexposed portions of the film (where the photoresist is crosslinkable in the exposed regions, i.e., negative tone). Preferably, the photoresist is positive tone based on a polymer having acid sensitive (deprotectable) groups, and the developer is preferably a metal-ion free tetraalkylammonium hydroxide solution, such as, for example, aqueous 0.26 N tetramethylammonium hydroxide. A pattern forms by developing.

Additionally, for positive resists, unexposed regions can be selectively removed by treatment with a suitable nonpolar solvent for negative tone development. See U.S. 2011/0294069 for suitable procedures for negative tone development of positive photoresists. Typical nonpolar solvents for negative tone development are organic developers, such as a solvent chosen from ketones, esters, hydrocarbons, and mixtures thereof, e.g. acetone, 2-hexanone, methyl acetate, butyl acetate, and terahydrofuran.

The photoresist may, when used in one or more such a pattern-forming processes, be used to fabricate electronic and optoelectronic devices such as memory devices, processor chips (CPU's), graphics chips, and other such devices.

Examples 1-19

Syntheses of Acid Generator Compounds

Example 1

Synthesis of 5-phenyl-5H-dibenzo[b,d]thiophenium 3-hydroxyadamantane-acetoxy-1,1,2,2-tetrafluorobutane-1-sulfonate

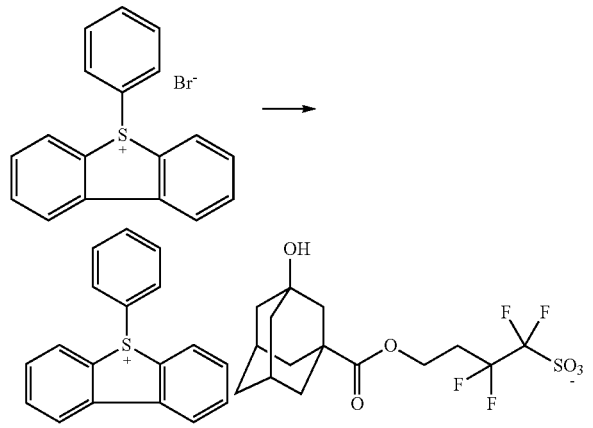

5-phenyl-5H-dibenzo[b,d]thiophenium bromide (28.0 g, 82.04 mmol) and 3-hydroxyadamantane-acetoxy-1,1,2,2-tetrafluorobutane-1-sulfonate-sodium salt (35.68 g, 83.7 mmol) were dissolved in dichloromethane (500 mL) and water (500 mL) and stirred at r.t. for 16 h. The dichloromethane layer was separated and the aqueous phase washed with dichloromethane (3×300 mL). The combined organic layers were washed with water (4×500 mL), concentrated in vacuo and residual water removed via azeotrope with acetonitrile (2×350 mL) to afford the title compound (54.00 g, 99%) as a white solid. $^1$H NMR (500 MHz, (CD$_3$)$_2$CO) 8.55 (d, J=8 Hz, 2H), 8.41 (d, J=8 Hz, 2H), 8.02 (dt, J=7.5, 0.5 Hz, 2H), 7.77-7.84 (m, 5H), 7.67 (t, J=7.5 Hz, 2H), 4.31 (t, J=6.5 Hz, 2H), 3.63 (s, 1OH), 2.71 (tt, J=14, 6.5 Hz, 2H), 1.52-1.80 (m, 12H).

Example 2

Synthesis of 5-phenyl-5H-dibenzo[b,d]thiophenium 1,1-difluoro-2-(methacryloyloxy)ethanesulfonate

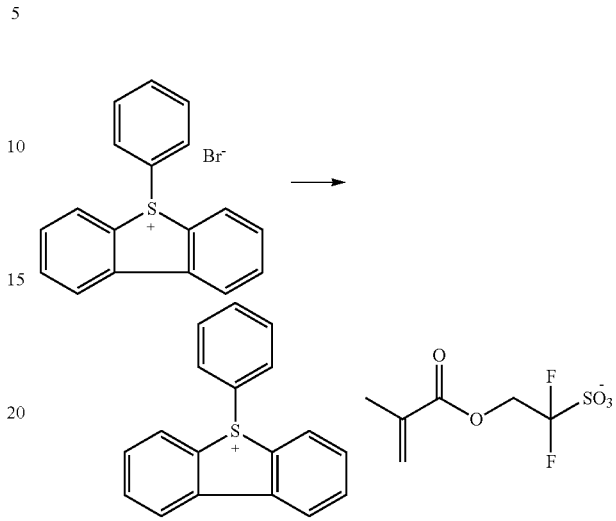

5-phenyl-5H-dibenzo[b,d]thiophenium bromide (80.0 g, 234 mmol) and triethylammonium 1,1-difluoro-2-(methacryloyloxy)ethanesulfonate (78.5 g, 238 mmol) were dissolved in H$_2$O (750 mL) and dichloromethane (750 mL) and stirred at r.t. for 18 h. The dichloromethane layer was separated and the aqueous phase washed with dichloromethane (3×500 mL). The combined organic layers were washed with water (3×1 L) and concentrated in vacuo to afford the title compound (109 g, 95%) as a white solid. $^1$H NMR (500 MHz, (CD$_3$)$_2$CO) δ: 8.56 (dd, J=7.5, 1 Hz, 2H), 8.42 (d, J=8 Hz, 2H), 8.05 (dt, J=8 Hz, 1 Hz, 2H), 7.77-7.87 (m, 5H), 7.69 (dt, J=8, 1 Hz, 2H), 6.14-6.16 (m, 1H), 5.66-5.69 (m, 1H), 4.75 (dd, J=15, 15 Hz, 2H), 1.93-1.94 (m, 3H).

Example 3

Synthesis of 1-ethylcyclopentyl 2-bromoacetate

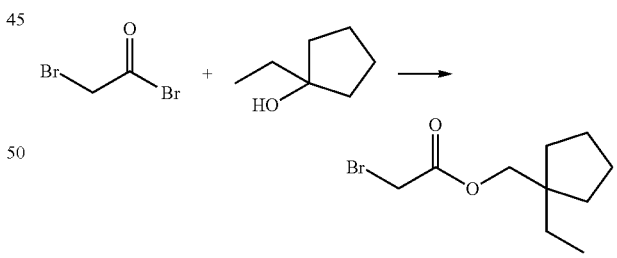

Pyridine (67.5 g, 0.854 mol) was added dropwise to a solution of ethylcyclopropanol (75.0 g, 675 mmol) in anhydrous dichloromethane (750 mL) under N$_2$ at 0° C. and stirred for 5 minutes. Bromoacetyl bromide (172 g, 74.4 mL, 854 mmol) in dichloromethane (75 mL) was added dropwise and the solution stirred at 0° C. for 20 h. The pyridinium bromide was filtered off, washed with dichloromethane (2×300 mL) and the solid pyridinium bromide discarded. The combined organic layers were washed with water (4×750 mL), and concentrated in vacuo. The crude oil was purified via of silica gel flash column chromatography (neutralized with TEA, 1:0 to 99:1 heptane:ethyl acetate).

After concentration, the oil was filtered to afford the title compound (130 g, 84%) as a light orange oil. NMR (500 MHz, (CD$_3$)$_2$SO) δ: 3.93 (s, 2H), 2.07-2.14 (m, 2H), 2.00 (q, J=7 Hz, 2H), 1.59-1.77 (m, 4H), 0.89 (t, J=7 Hz, 3H).

Example 4

Synthesis of 5-(4-hydroxy-3,5-dimethylphenyl)-5H-dibenzo[b,d]thiophenium bromide

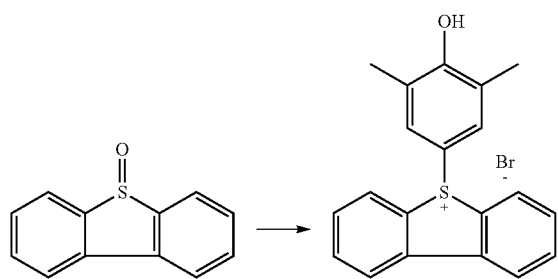 [SMILES: O=S1c2ccccc2-c2ccccc21 ; Cc1cc(-[s+]2c3ccccc3c3ccccc32)cc(C)c1O ; Br]

Eaton's Reagent (100 mL) was added dropwise to a solution of dibenzothiophene oxide (15.0 g, 74.9 mmol) and 2,6-dimethylphenol (9.15 g, 74.9 mmol) in dichloromethane (200 mL) at 0° C. The reaction was warmed to r.t. and stirred for 4 h, then cooled to 0° C. and quenched with the slow addition of water (200 mL) keeping the reaction temperature below 20° C. The aqueous phase was extracted with ethyl acetate (3×100 mL) and potassium bromide (17.9 g, 0.150 mmol) in water (50 mL) was added to the aqueous layer under vigorous stirring. The slurry was stirred at r.t. for 1 h, filtered and washed with water (3×200 mL), MTBE (3×200 mL) and the residue dried in vacuo to afford the title compound (10.1 g, 35%) as an off-white solid. $^1$H NMR (300 MHz, (CD$_3$)$_2$CO) δ: 9.77 (brs, 10H), 8.52 (d, J=8.1 Hz, 2H), 8.27 (8.1 Hz, 2H), 7.95 (t, J=7.8 Hz, 2H), 7.74 (t, J=7.8 Hz, 2H), 7.20 (s, 2H), 2.12 (s, 6H).

Example 5

Synthesis of 5-(4-(2-(1-ethylcyclopentyloxy)-2-oxoethoxy)-3,5-dimethylphenyl)-5H-dibenzo[b,d]thiophenium bromide

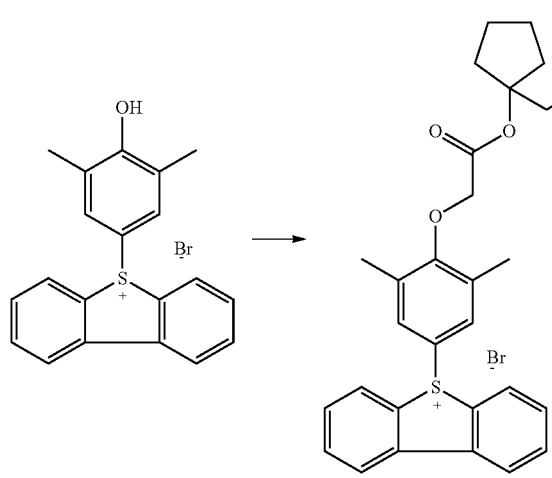

1-ethylcyclopentyl 2-bromoacetate (4.03 g, 17.1 mmol, 1.1 eq) was added dropwise to a solution of 5-(4-hydroxy-3,5-dimethylphenyl)-5H-dibenzo[b,d]thiophenium bromide (6.00 g, 15.6 mmol) and cesium carbonate (10.15 g, 31.1 mmol, 2 eq) in dimethylformamide (150 mL) under N$_2$ at 0° C. The solution was slowly warmed to r.t. and stirred for 16 h. The reaction mixture was diluted with water (400 mL) and dichloromethane (400 mL). The organic layer was separated and the aqueous layer extracted with dichloromethane (4×150 mL). The combined organic layers were extracted with water (2×300 mL), dried (Na$_2$SO$_4$) and concentrated to the remaining DMF (~100 mL). This non-viscous solution was slowly poured onto MTBE (700 mL) under vigorous stirring. The precipitate was filtered, washed with MTBE (3×200 mL) and the residue dried in vacuo to afford the title compound (7.92 g, 94%) as a white solid. $^1$H NMR (500 MHz, d-DMSO) δ: 8.51 (d, J=8 Hz, 2H), 8.32 (d, J=7.5 Hz, 2H), 7.96 (t, J=7.5 Hz, 2H), 7.75 (t, J=7.5 Hz, 2H), 7.31 (s, 2H), 4.51 (s, 2H), 2.21 (s, 6H), 1.93-2.03 (m, 2H), 1.92 (q, J=7 Hz, 2H), 1.49-1.69 (m, 6H), 0.79 (t, J=7 Hz, 3H).

Example 6

Synthesis of 5-(4-(2-(1-ethylcyclopentyloxy)-2-oxoethoxy)-3,5-dimethylphenyl)-5H-dibenzo[b,d]thiophenium 3-hydroxyadamantane-acetoxy-1,1,2,2-tetrafluorobutane-1-sulfonate

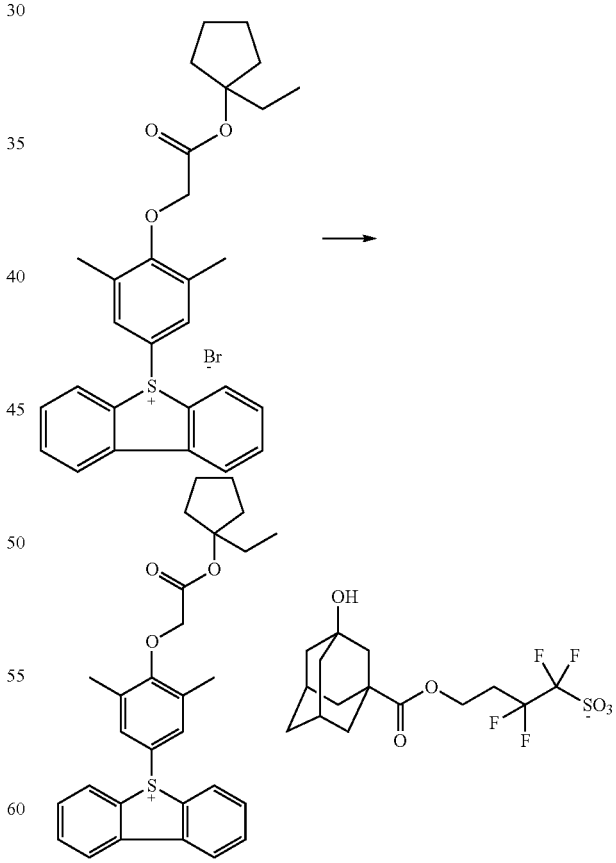

5-(4-(2-(1-ethylcyclopentyloxy)-2-oxoethoxy)-3,5-dimethylphenyl)-5H-dibenzo[b,d]thiophenium bromide (2.00 g, 3.71 mmol) and sodium 3-hydroxyadamantane-acetoxy-1,1,2,2-tetrafluorobutane-1-sulfonate (1.61 g, 3.78 mmol) were dissolved in dichloromethane (100 mL) and water (100 mL) and stirred at r.t. overnight. The dichloromethane layer was separated and the aqueous phase washed with dichloromethane (3×100 mL). The combined organic layers were washed with water (4×200 mL), concentrated in vacuo and residual water removed via azeotrope with acetonitrile (2×200 mL) to afford the title compound (2.90 g, 91%) as a white solid. $^1$H NMR (500 MHz, (CD$_3$)$_2$CO) δ: 8.52 (d, J=8 Hz, 2H), 8.34 (d, J=8.5 Hz, 2H), 8.01 (t, J=7.5 Hz, 2H), 7.08 (t, J=7.5 Hz, 2H), 7.51 (s, 2H), 4.55 (s, 2H), 4.32 (t, J=6.5 Hz, 2H), 3.60 (brs, OH), 2.72 (tt, J=14, 6.5 Hz, 2H), 2.29 (s, 6H), 2.12-2.20 (m, 2H), 2.00 (q, J=7 Hz, 2H), 1.50-1.82 (m, 12H), 0.84 (t, J=7 Hz, 3H).

Example 7

Synthesis of 5-(4-(2-(1-ethylcyclopentyloxy)-2-oxoethoxy)-3,5-dimethylphenyl)-5H-dibenzo[b,d]thiophenium 4-((4R)-4-((8R,9S,10S,13R,14S,17R)-10,13-dimethyl-3,7,12-trioxohexadecahydro-1H-cyclopenta[a]phenanthren-17-yl)pentanoyloxy)-1,1,2,2-tetrafluorobutane-1-sulfonate 5-(4-(2-(1-ethylcyclopentyloxy)-2-oxoethoxy)-3,5-dimethylphenyl)-5H-dibenzo[b,d]thiophenium bromide (4.20 g, 7.79 mmol) and sodium 4-((4R)-4-((8R,9S,10S,13R,14S,17R)-10,13-dimethyl-3,7,12-trioxohexadecahydro-1H-cyclopenta[a]phenanthren-17-yl)pentanoyloxy)-1,1,2,2-tetrafluorobutane-1-sulfonate (4.78 g, 7.56 mmol) were dissolved in dichloromethane (225 mL) and water (225 mL) and stirred at room temperature overnight. The dichloromethane layer was separated and the aqueous phase washed with dichloromethane (3×250 mL). The combined organic layers were washed with water (4×250 mL), concentrated in vacuo and residual water removed via azeotrope with acetonitrile (2×250 mL) to afford the title compound (6.48 g, 80%) as a white solid. $^1$H NMR (500 MHz, (CD$_3$)$_2$CO) δ: 8.53 (d, J=8 Hz, 2H), 8.37 (d, J=8 Hz, 2H), 8.04 (t, J=7.5 Hz, 2H), 7.85 (t, J=7.5 Hz, 2H), 7.52 (s, 2H), 4.57 (s, 2H), 4.32 (t, J=7 Hz, 2H), 3.06-3.17 (m, 3H), 2.95 (t, J=12.5 Hz, 1H), 2.66-2.83 (m, 3H), 2.2-2.54 (m, 8H), 1.57-2.14 (m, 13H), 1.48 (s, 3H), 1.25-1.41 (m, 7H), 1.90-1.12 (m, 6H), 0.82-0.89 (m, 9H).

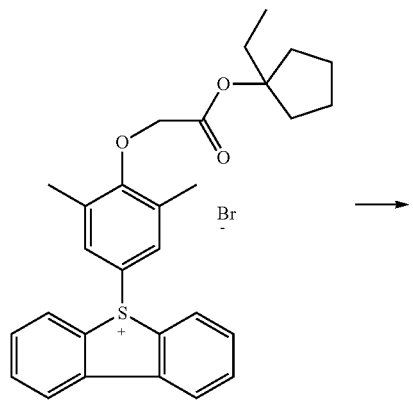

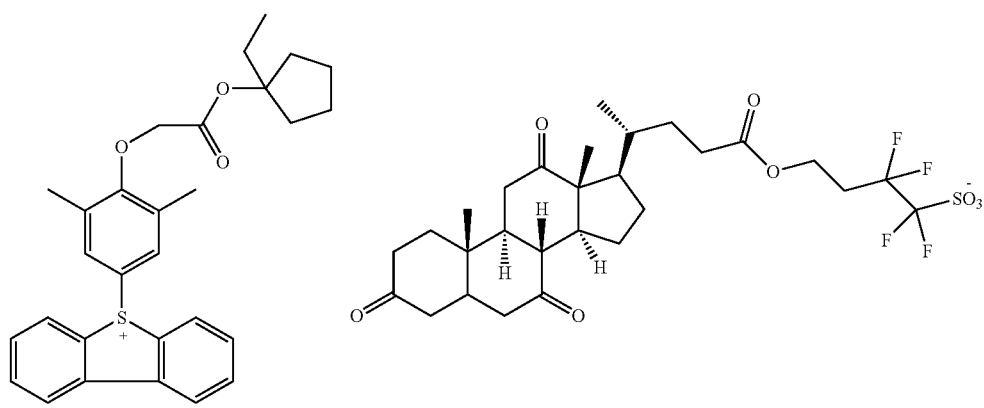

Example 8

Synthesis of 5-(4-(2-(1-ethylcyclopentyloxy)-2-oxoethoxy)-3,5-dimethylphenyl)-5H-dibenzo[b,d]thiophenium 1,1-difluoro-2-(methacryloyloxy)ethanesulfonate

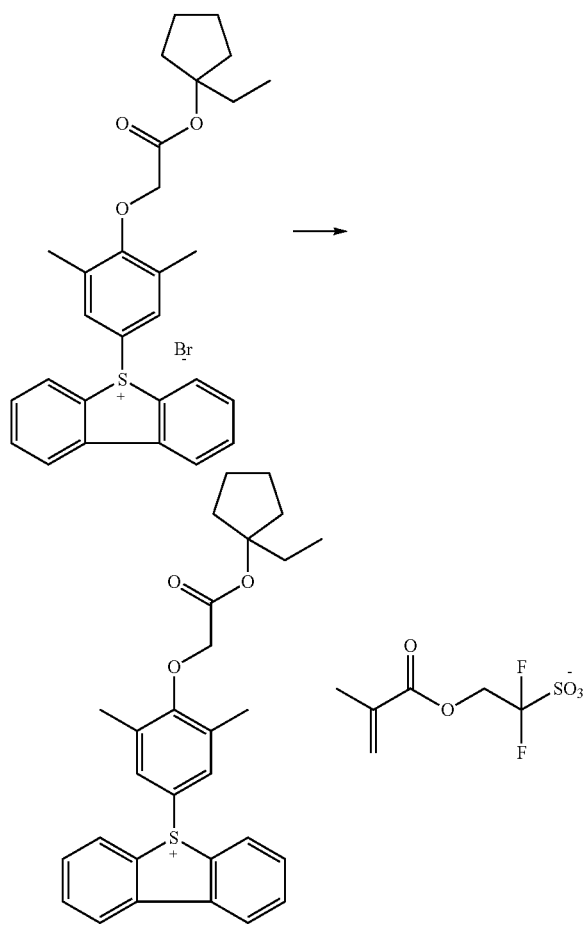

5-(4-(2-(1-ethylcyclopentyloxy)-2-oxoethoxy)-3,5-dimethylphenyl)-5H-dibenzo[b,d]thiophenium bromide (20.0 g, 37.1 mmol) and triethylammonium 1,1-difluoro-2-(methacryloyloxy)ethanesulfonate (1.1 eq, 40.8 mmol, 13.5 g) were dissolved in dichloromethane (250 mL) and water (250 mL) and stirred at r.t. overnight. The dichloromethane layer was separated and the aqueous phase washed with dichloromethane (3×250 mL). The combined organic layers were washed with water (4×250 mL), concentrated in vacuo and residual water removed via azeotrope with acetonitrile (2×250 mL) to afford the title compound (23.8 g, 93%) as a white solid. $^1$H NMR (300 MHz, (CD$_3$)$_2$CO) δ: 8.53 (d, J=7.8 Hz, 2H), 8.36 (d, J=7.8 Hz, 2H), 8.04 (t, J=7.5 Hz, 2H), 7.83 (t, J=7.8 Hz, 2H), 7.51 (visual s, 2H), 6.14-6.16 (m, 2H), 5.66-5.69 (m, 2H), 4.75 (dd, J=15.6, 15.6 Hz, 2H), 4.57 (s, 2H), 2.30 (s, 6H), 2.03-2.11 (m, 2H), 2.02 (q, J=7.8 Hz, 2H), 1.93-1.95 (m, 3H), 1.55-1.6 (m, 6H), 0.84 (t, J=7.5 Hz, 3H).

Example 9

Synthesis of 5-(5-carboxy-2-methoxyphenyl)-5H-dibenzo[b,d]thiophenium iodide

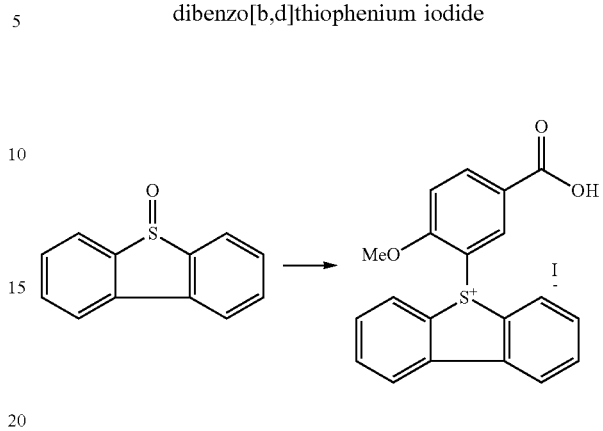

Dibenzothiophene oxide (57 g, 285 mmol) and 4-methoxybenzoic acid (47.7 g, 314 mmol, 1.1 eq) were suspended in dichloromethane (400 mL) and cooled to 0° C. where Eaton's Reagent (285 mL) was added dropwise. The solution was taken off ice and stirred overnight at r.t. The reaction mixture was cooled back to 0° C. and quenched with the slow addition of water (800 mL), followed by ethyl acetate (500 mL). The precipitate was filtered off and the layers separated. The aqueous layer was extracted with ethyl acetate (2×500 mL) and the combined organic layers were washed with water (500 mL). Sodium iodide (341.6 g, 2.28 mol, 4 eq) in water (500 mL) was slowly poured onto the combined aqueous layers. Additional water was slowly added until precipitation of a viscous oil stopped. The crude oil was recrystallized from acetone afford the title compound (72.0 g, 55%) as a white solid. $^1$H NMR (300 MHz, (d-DMSO) δ: 12.0-13.0 (brs, 1H), 8.54 (d, J=7.8 Hz, 2H), 8.35 (d, J=8.1 Hz, 2H), 8.21 (dd, J=8.7, 2.1 Hz, 1H), 7.99 (t, J=7.8 Hz, 2H), 7.79 (t, J=7.8 Hz, 2H), 7.51 (d, J=8.7 Hz, 1H), 7.44 (d, J=2.1 Hz, 1H), 4.08 (s, 3H).

Example 10

Synthesis of 5-(5-((2-(1-ethylcyclopentyloxy)-2-oxoethoxy)carbonyl)-2-methoxyphenyl)-5H-dibenzo[b,d]thiophenium iodide

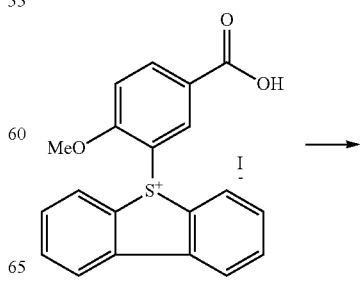

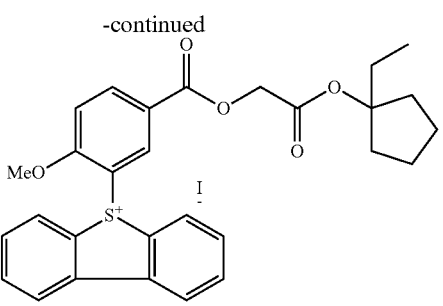

5-(5-carboxy-2-methoxyphenyl)-5H-dibenzo[b,d]thiophenium iodide (40.7 g, 88.0 mmol) and cesium carbonate (39.1 g, 0.120 mol, 1.5 eq) were suspended in dimethylformamide (500 mL) and cooled to 0° C. where 1-ethylcyclopentyl 2-bromoacetate (22.8 g, 96.8 mmol, 1.1 eq) was added dropwise. The reaction was taken off ice, stirred for 4 h, diluted with water (1 L) and extracted with dichloromethane (4×500 mL). The aqueous layer was discarded. The combined organic layers were washed with water (3×500 mL) and the combined aqueous extracts were back extracted with dichloromethane (2×400 mL). The combined organic layers were concentrated down to the residual dimethylformamide, poured slowly onto MTBE (1.75 L) and vigorously stirring to form a precipitate that was filtered and washed with MTBE (2×500 mL) to afford the title compound (52.9 g, 97%) as a white solid. $^1$H NMR (300 MHz, (CD$_3$)$_2$CO) δ: 8.52-8.59 (m, 4H), 8.38 (dd, J=8.7, 2.1 Hz, 1H), 8.05 (t, J=8.1 Hz, 2H), 7.96 (d, J=2.1 Hz, 1H), 7.85 (t, J=8.1 Hz, 2H), 7.60 (d, J=8.1 Hz, 1H), 4.75 (s, 2H), 4.12 (s, 3H), 2.02-2.12 (m, 2H), 1.97 (q, J=6.6 Hz, 2H), 1.55-1.70 (m, 6H), 0.86 (t, J=6.6 Hz, 3H).

Example 11

5-(5-((2-(1-ethylcyclopentyloxy)-2-oxoethoxy)carbonyl)-2-methoxyphenyl)-5H-dibenzo[b,d]thiophenium 3-hydroxyadamantane-acetoxy-1,1,2,2-tetrafluorobutane-1-sulfonate

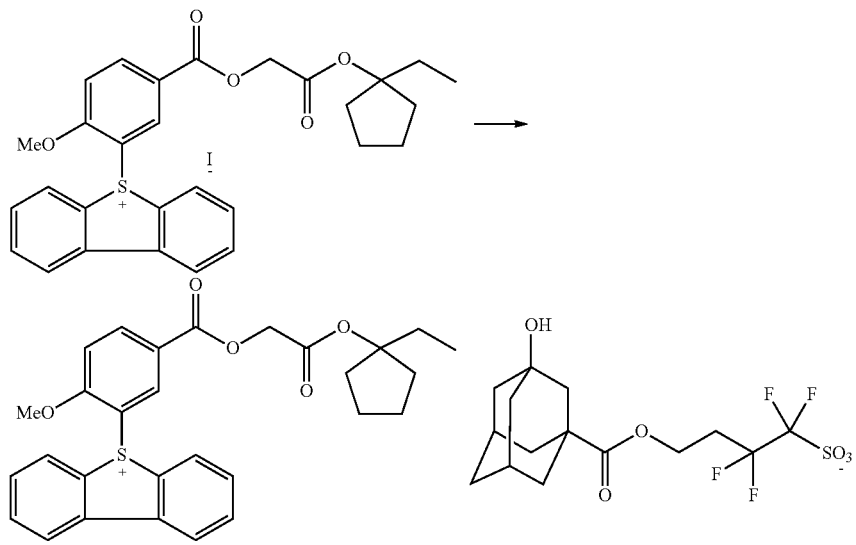

5-(5-((2-(1-ethylcyclopentyloxy)-2-oxoethoxy)carbonyl)-2-methoxyphenyl)-5H-dibenzo[b,d]thiophenium iodide (10.0 g, 16.2 mmol) and sodium 3-hydroxyadamantane-acetoxy-1,1,2,2-tetrafluorobutane-1-sulfonate (7.26 g, 17.0 mmol, 1.05 eq) were dissolved in dichloromethane (200 mL) and water (200 mL) and stirred at r.t. overnight. The dichloromethane layer was separated and the aqueous phase washed with dichloromethane (3×250 mL). The combined organic layers were washed with water (3×250 mL), concentrated in vacuo and azeotroped with acetonitrile (2×100 mL) to afford the title compound (13.3 g, 92%) as a white solid. $^1$H NMR (500 MHz, (CD$_3$)$_2$CO) δ: 8.56 (d, J=8 Hz, 2H), 8.44 (d, J=8 Hz, 2H), 8.40 (dd, J=9, 2 Hz, 1H), 8.06 (t, J=8 Hz, 2H), 7.99 (d, J=2 Hz, 1H), 7.86 (t, J=8 Hz, 2H), 7.60 (d, J=9 Hz, 1H), 4.76 (s, 2H), 4.31 (t, J=6.5 Hz, 2H), 4.10 (s, 3H), 3.56 (s, 1H), 2.69 (tt, J=18.5, 7 Hz, 2H), 2.01-2.07 (m, 2H), 1.97 (q, J=7.5 Hz, 2H), 1.55-1.81 (m, 18H), 0.86 (t, J=7.5 Hz, 3H).

Example 12

Synthesis of 5-(5-((2-(1-ethylcyclopentyloxy)-2-oxoethoxy)carbonyl)-2-methoxyphenyl)-5H-dibenzo[b,d]thiophenium 4-((4R)-4-((8R,9S,10S,13R,14S,17R)-10,13-dimethyl-3,7,12-trioxohexadecahydro-1H-cyclopenta[a]phenanthren-17-yl)pentanoyloxy)-1,1,2,2-tetrafluorobutane-1-sulfonate

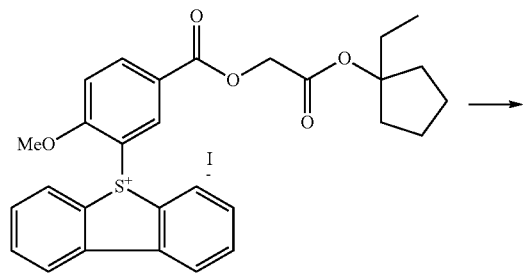

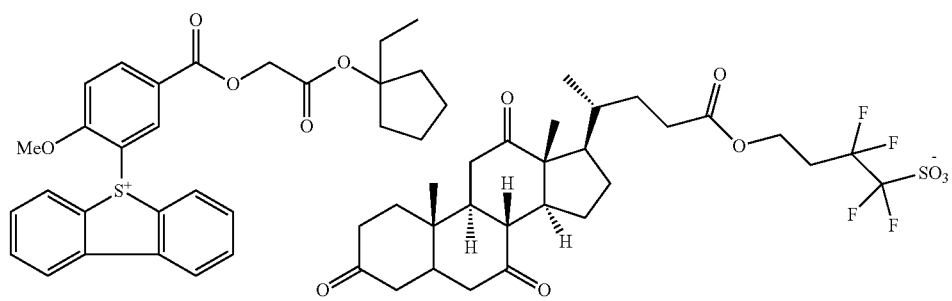

5-(5-((2-(1-ethylcyclopentyloxy)-2-oxoethoxy)carbonyl)-2-methoxyphenyl)-5H-dibenzo[b,d]thiophenium iodide (5.00 g, 8.80 mmol) and sodium 4-((4R)-4-((8R,9S,10S,13R,14S,17R)-10,13-dimethyl-3,7,12-trioxohexadecahydro-1H-cyclopenta[a]phenanthren-17-yl)pentanoyloxy)-1,1,2,2-tetrafluorobutane-1-sulfonate (5.84 g, 9.24 mmol) were dissolved in dichloromethane (250 mL) and water (250 mL) and stirred at r.t. overnight. The dichloromethane layer was separated and the aqueous phase washed with dichloromethane (3×250 mL). The combined organic layers were washed with water (4×250 mL), concentrated in vacuo and residual water removed via azeotrope with acetonitrile (2×250 mL) to afford the title compound (8.10 g, 84%) as a white solid. $^1$H NMR (500 MHz, (CD$_3$)$_2$CO) δ: 8.56 (d, J=7.5 Hz, 2H), 8.44 (d, J=8.5 Hz, 2H), 8.40 (dd, J=8, 2 Hz, 1H), 8.06 (t, J=8 Hz, 2H), 7.99 (vis s, 1H), 7.86 (t, J=8 Hz, 2H), 7.60 (d, J=8.5 Hz, 1H), 4.75 (s, 2H), 4.31 (t, J=6.5 Hz, 2H), 4.10 (s, 3H), 3.06-3.17 (m, 2H), 2.94 (t, J=13 Hz, 1H), 2.64-2.82 (m, 4H), 2.20-2.52 (m, 7H), 1.73-2.10 (m, 14H), 1.55-1.69 (m, 7H), 1.48 (s, 3H), 1.28-1.39 (m, 5H), 1.11 (s, 3H), 0.83-0.89 (m, 6H).

Example 13

5-(5-((2-(1-ethylcyclopentyloxy)-2-oxoethoxy)carbonyl)-2-methoxyphenyl)-5H-dibenzo[b,d]thiophenium 1,1-difluoro-2-(methacryloyloxy)ethanesulfonate

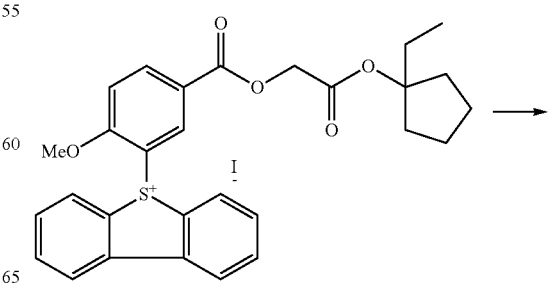

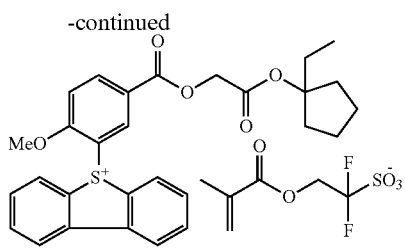

5-(5-((2-(1-ethylcyclopentyloxy)-2-oxoethoxy)carbonyl)-2-methoxyphenyl)-5H-dibenzo[b,d]thiophenium iodide (10.0 g, 16.2 mmol) and triethylammonium 1,1-difluoro-2-(methacryloyloxy)ethanesulfonate (5.64 g, 17.0 mmol, 1.05 eq) were dissolved in dichloromethane (200 mL) and water (200 mL) and stirred at r.t. overnight. The dichloromethane layer was separated and the aqueous phase washed with dichloromethane (3×250 mL). The combined organic layers were washed with water (3×250 mL), concentrated in vacuo and azeotroped with acetonitrile (2×100 mL) to afford the title compound (10.1 g, 86%) as a white hydroscopic solid. $^1$H NMR (300 MHz, (d-DMSO) δ: 8.52 (d, J=7.8 Hz, 2H), 8.35 (d, J=7.8 Hz, 2H), 8.27 (dd, J=8.1, 2.1 Hz, 1H), 7.98 (t, J=7.8 Hz, 2H), 7.78 (t, J=7.8 Hz, 2H), 7.55 (d, J=2.1 Hz, 1H), 7.54 (d, J=7.8 Hz, 1H), 6.09-6.13 (m, 1H), 5.76-5.79 (m, 1H), 4.74 (s, 2H), 4.62 (dd, J=15.6, 15.6 Hz, 2H), 4.05 (s, 3H), 1.83-1.98 (m, 7H), 1.45-1.65 (m, 6H), 0.79 (t, J=6.6 Hz, 3H).

Example 14

2-phenylpropan-2-yl 2-bromoacetate

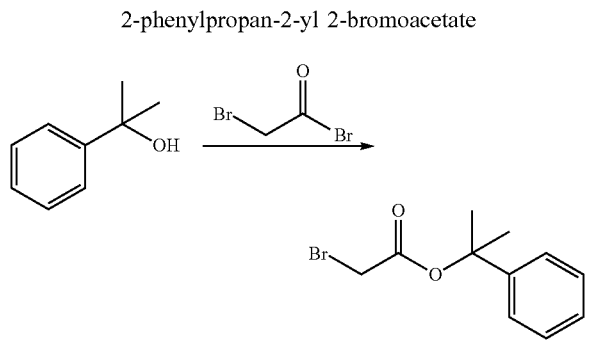

Pyridine (3.84 mL, 47.7 mmol) followed by bromoacetyl bromide (4.16 mL, 47.7 mmol) was added to a solution of 2-phenylpropan-2-ol (5.00 g, 36.7 mmol) in dichloromethane (100 mL) at 0° C., warmed to r.t. and stirred overnight. The reaction mixture was washed with water (3×100 mL), saturated aqueous sodium bicarbonate (3×100 mL), water (2×100 mL), dried (Na$_2$SO$_4$) and concentrated. The crude residue was purified by silica gel flash column chromatography (neutralized with TEA, heptanes) to afford the title compound (2.8 g (non-optimized), 30%) as a colorless oil. $^1$H NMR (300 MHz, ((CD$_3$)$_2$CO) δ: 7.44 (d, J=7.2 Hz, 2H), 7.34 (t, J=7.2 Hz, 2H), 7.25 (t, J=7.2 Hz, 1H), 4.01 (s, 2H), 1.78 (s, 6H).

Example 15

5-(3,5-dimethyl-4-(2-oxo-2-(2-phenylpropan-2-yloxy)ethoxy)phenyl)-5H-dibenzo[b,d]thiophenium bromide

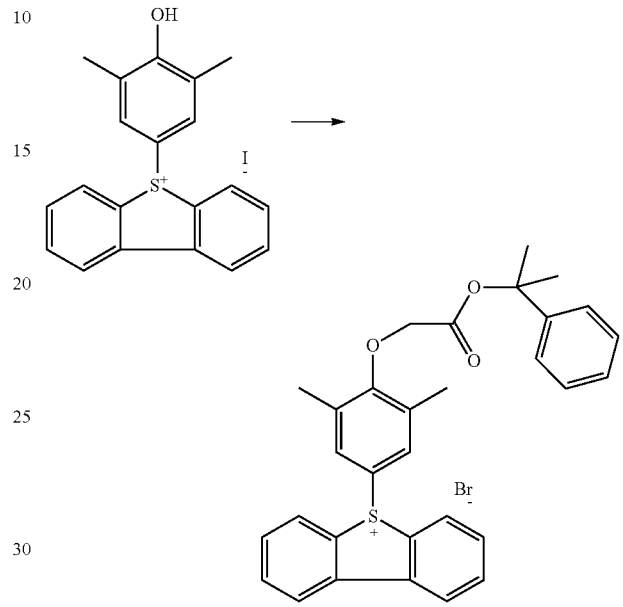

2-phenylpropan-2-yl 2-bromoacetate (1.96 g, 7.63 mmol) was added to a solution of 5-(4-hydroxy-3,5-dimethylphenyl)-5H-dibenzo[b,d]thiophenium iodide (3.00 g, 6.94 mmol) and cesium carbonate (2.94 g, 9.02 mmol) in DMF (40 mL) at 0° C., warmed to r.t. and stirred overnight. The reaction mixture was diluted with water (200 mL) and washed with DCM (3×200 mL). The organic layers were washed with water (3×300 mL), concentrate and poured onto MTBE. The precipitate was filtered and dried to afford the title compound (3.80 g, 97%) as a white solid. $^1$H NMR (300 MHz, ((CD$_3$)$_2$SO) δ: 8.52 (d, J=7.5 Hz, 2H), 8.33 (d, J=7.5 Hz, 2H), 7.96 (t, J=7.2 Hz, 2H), 7.5 (d, J=7.9 Hz, 2H), 7.20-7.39 (m, 5H), 4.61 (s, 2H), 2.19 (s, 6H), 1.71 (s, 6H).

Example 16

5-(3,5-dimethyl-4-(2-oxo-2-(2-phenylpropan-2-yloxy)ethoxy)phenyl)-5H-dibenzo[b,d]thiophenium 3-hydroxyadamantane-acetoxy-1,1,2,2-tetrafluorobutane-1-sulfonate

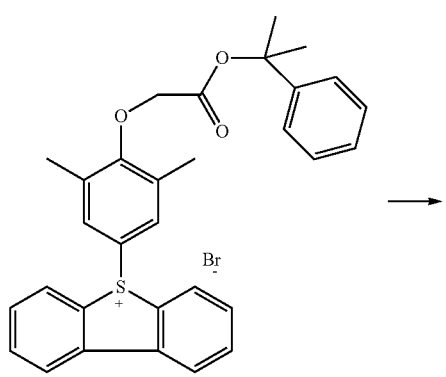

-continued

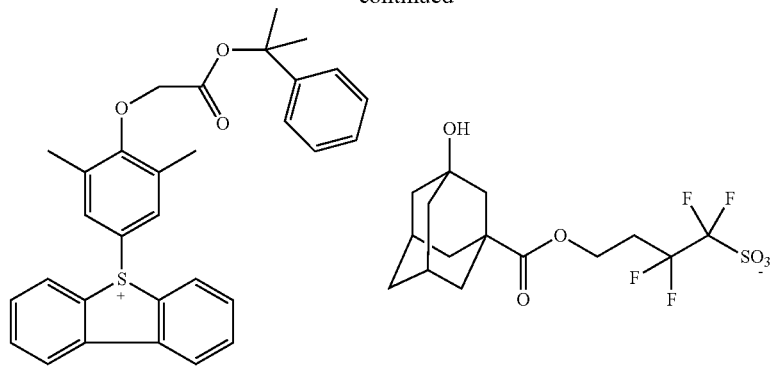

5-(3,5-dimethyl-4-(2-oxo-2-(2-phenylpropan-2-yloxy) ethoxy)phenyl)-5H-dibenzo[b,d]thiophenium bromide (1.8 g, 3.21 mmol) and sodium 3-hydroxyadamantane-acetoxy-1,1,2,2-tetrafluorobutane-1-sulfonate (1.44 g, 3.37 mmol) were dissolved in dichloromethane (100 mL) and water (100 mL) and stirred at r.t. overnight. The dichloromethane layer was separated and the aqueous phase washed with dichloromethane (3×100 mL). The combined organic layers were washed with water (6×200 mL) and concentrated in vacuo to afford the title compound (2.44 g, 86%) as a white solid. $^1$H NMR (500 MHz, ((CD$_3$)$_2$SO) δ: 8.53 (d, J=8 Hz, 2H), 8.35 (d, J=8 Hz, 2H), 8.03 (t, J=7 Hz, 2H), 7.83 (d, J=8 Hz, 2H), 7.51 (s, 2H), 7.40 (d, J=8 Hz, 2H), 7.31 (dt, J=8, 0.5 Hz, 2H), 7.24 (dt, J=7.5, 1 Hz, 1H), 4.65 (s, 2H), 4.31 (t, J=6.5 Hz, 2H), 2.80-2.82 (m, 2H), 2.65 (tt, J=14, 6.5 Hz, 2H), 2.29 (s, 6H), 1.72-1.81 (m, 10H), 1.65-1.67 (m, 4H), 1.56-1.59 (m, 2H).

Example 17

Synthesis of 5-(3,5-dimethyl-4-(2-oxo-2-(2-phenylpropan-2-yloxy)ethoxy)phenyl)-5H-dibenzo[b,d] thiophenium 4-((4R)-4-((8R,9S,10S,13R,14S,17R)-10,13-dimethyl-3,7,12-trioxohexadecahydro-1H-cyclopenta[a]phenanthren-17-yl)pentanoyloxy)-1,1,2,2-tetrafluorobutane-1-sulfonate

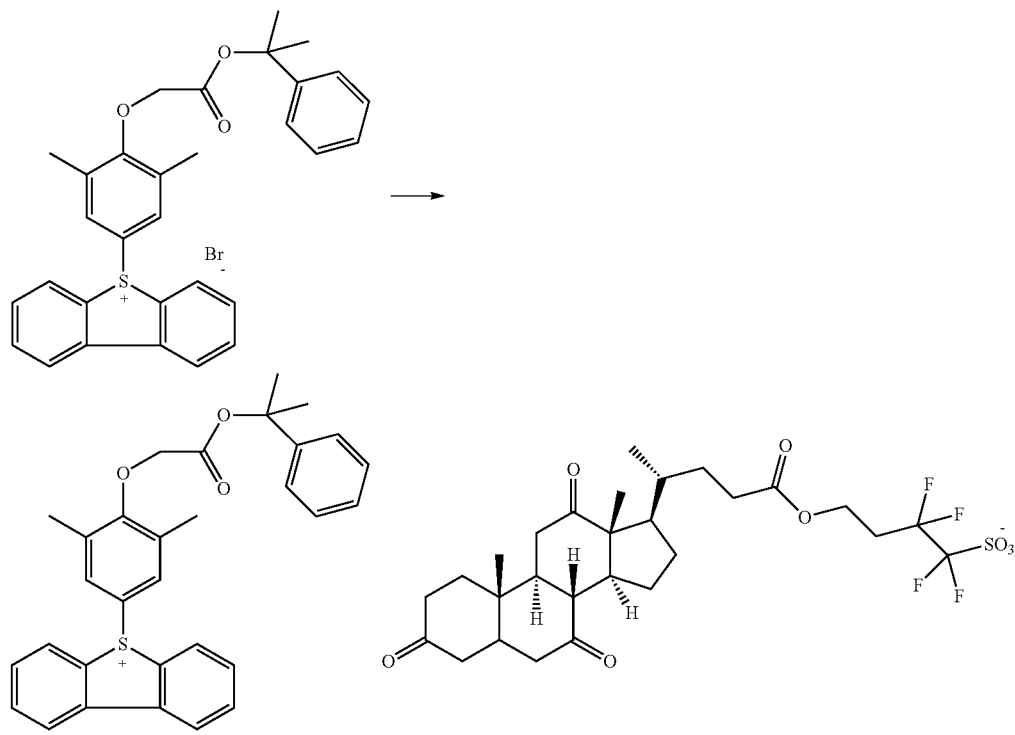

5-(3,5-dimethyl-4-(2-oxo-2-(2-phenylpropan-2-yloxy) ethoxy)phenyl)-5H-dibenzo[b,d]thiophenium bromide (1.8 g, 3.21 mmol) and sodium 4-((4R)-4-((8R,9S,10S,13R,14S,17R)-10,13-dimethyl-3,7,12-trioxohexadecahydro-1H-cyclopenta[a]phenanthren-17-yl)pentanoyloxy)-1,1,2,2-tetrafluorobutane-1-sulfonate (2.13 g, 3.37 mmol) were dissolved in dichloromethane (50 mL) and water (50 mL) and stirred at room temperature overnight. The dichloromethane layer was separated and the aqueous phase washed with dichloromethane (3×50 mL). The combined organic layers were washed with water (4×100 mL), concentrated in vacuo and residual water removed via azeotrope with acetonitrile (2×100 mL) to afford the title compound (2.77 g, 79%) as a white solid. $^1$H NMR (500 MHz, (CD$_3$)$_2$CO) δ: 8.53 (d, J=8 Hz, 2H), 8.35 (d, J=8 Hz, 2H), 8.04 (t, J=7.5 Hz, 2H), 7.83 (t, J=7.5 Hz, 2H), 7.50 (s, 2H), 7.40 (d, J=8 Hz, 2H), 7.31 (t, J=8 Hz, 2H), 7.24 (t, J=8 Hz, 1H), 4.65 (s, 2H), 4.32 (t, J=6.5 Hz, 2H), 3.05-3.17 (m, 2H), 2.94 (t, J=12.5 Hz, 1H), 2.64-2.82 (m, 5H), 2.21-2.53 (m, 12H), 1.72-2.10 (m, 17H), 1.56-1.65 (m, 1H), 1.47 (s, 3H), 1.28-1.38 (m, 5H), 1.10 (s, 3H), 0.83-0.87 (m, 3H).

Example 18

Synthesis of 5-(3,5-dimethyl-4-(2-oxo-2-(2-phenyl-propan-2-yloxy)ethoxy)phenyl)-5H-dibenzo[b,d]thiophenium 1,1-difluoro-2-(methacryloyloxy)ethanesulfonate

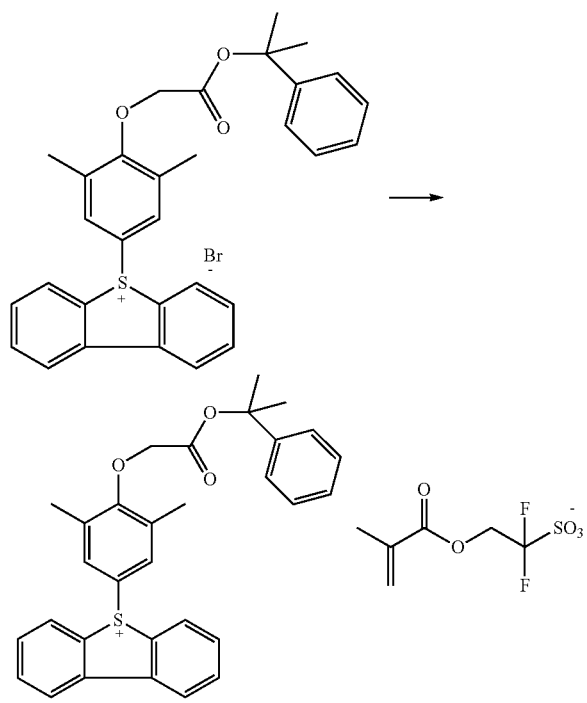

5-(3,5-dimethyl-4-(2-oxo-2-(2-phenylpropan-2-yloxy) ethoxy)phenyl)-5H-dibenzo[b,d]thiophenium bromide (7.00 g, 12.5 mmol) and triethylammonium 1,1-difluoro-2-(methacryloyloxy)ethanesulfonate (4.21 g, 12.7 mmol) were dissolved in dichloromethane (100 mL) and water (100 mL) and stirred at room temperature overnight. The dichloromethane layer was separated and the aqueous phase washed with dichloromethane (3×100 mL). The combined organic layers were washed with water (4×100 mL), concentrated in vacuo and residual water removed via azeotrope with acetonitrile (2×100 mL) to afford the title compound (7.07 g, 80%) as a white solid. $^1$H NMR (300 MHz, (CD$_3$)$_2$CO) δ: 8.53 (d, J=7.8 Hz, 2H), 8.37 (d, J=7.8 Hz, 2H), 8.03 (t, J=7.8 Hz, 2H), 7.82 (t, J=7.8 Hz, 2H), 7.52 (s, 2H), 7.40 (d, J=8.1 Hz, 2H), 7.32 (t, J=8.1 Hz, 2H), 7.26 (t, J=8.1 Hz, 1H), 6.12-6.19 (m, 1H), 5.68-5.71 (m, 1H), 4.76 (t, J=15.6 Hz, 2H), 4.66 (s, 2H), 2.28 (s, 6H), 1.94 (s, 3H), 1.77 (s, 6H).

Example 19

Preparation of Polymer with Acid Generator Units

Heel solution was made by dissolving 2-phenylpropan-2-yl methacrylate (0.39 g), 2-oxotetrahydrofuran-3-yl methacrylate (0.33 g), 3,5-bis(1,1,1,3,3,3-hexafluoro-2-hydroxypropan-2-yl)cyclohexyl methacrylate (0.57 g) and the monomer of Example 8 (0.31 g) in 12.81 g acetonitrile/tetrahydrofuran (2/1 v/v). Feed solution was prepared by dissolving 2-phenylpropan-2-ylmethacrylate (185.54 g, 0.967 mol), 2-oxotetrahydrofuran-3-yl methacrylate (204.27, 1.26 mol), 3,5-bis(1,1,1,3,3,3-hexafluoro-2-hydroxypropan-2-yl)cyclohexyl methacrylate (127.98 g, 0.29 mol) and the monomer of Example 8 (81.5 g, 0.132 mol) in 606 g ethyl lactate:γ-butryl lactone (30/70 v/v). Initiator solution was prepared by dissolving 65.96 g initiator (V-65) in 66 g acetonitrile/tetrahydrofuran (2/1 v/v). The polymerization was carried out in a 2 L 3-neck round bottom flask fitted with a water condenser and a thermometer to monitor the reaction in the flask. The contents were stirred using an overhead stirrer. The reactor was charged with the heel solution and the contents were heated to 75° C. The feed solution and the initiator solution were fed into the reactor using syringe pump over a 4 hour time period. The contents were then stirred for additional 2 hours, whereby, the reaction was quenched using hydroquinone (2.0 g). The contents were cooled to room temperature and precipitated twice out of 10× (by weight) IPE/MeOH 95/5 (w/w). The polymer obtained was dried in vacuo after each precipitation step at 50° C. for 24 hours to yield 500 g polymer Example 20

Further Preparation of Polymer with Acid Generator Units

The same process used for Example 19 was used in the preparation of polymer, except using the monomer of Example 2 was used in place of the monomer of Example 8.

Example 21

Further Preparation of Polymer with Acid Generator Units

The same process used for Example 19 was used in the preparation of polymer, except using the monomer of Example 13 was used in place of the monomer of Example 8.

Example 22

Preparation of Polymer without Acid Generator Units

Heel solution was made by dissolving 2-phenylpropan-2-yl methacrylate (1.94 g), 2-oxotetrahydrofuran-3-yl methacrylate (1.7 g), 3,5-bis(1,1,1,3,3,3-hexafluoro-2-hydroxypropan-2-yl)cyclohexyl methacrylate (2.81 g) in 72 g ethyl lactate:☐-butryl lactone (30/70 v/v). Feed solution was prepared by dissolving 2-phenylpropan-2-yl methacrylate (33.08 g), 2-oxotetrahydrofuran-3-yl methacrylate (35.97), 3,5-bis(1,1,1,3,3,3-hexafluoro-2-hydroxypropan-2-yl)cyclohexyl methacrylate (23.91 g) 94 g ethyl lactate:☐-butryl lactone (30/70 v/v). Initiator solution was prepared by dissolving 11 g initiator (V-65) in 11 g acetonitrile/tetrahydrofuran (2/1 v/v). The polymerization was carried out in a 2 L 3-neck round bottom flask fitted with a water condenser and a thermometer to monitor the reaction in the flask. The contents were stirred using an overhead stirrer. The reactor was charged with the heel solution and the contents were heated to 75° C. The feed solution and the initiator solution were fed into the reactor using syringe pump over a 4 hour time period. The contents were then stirred for additional 2 hours, whereby, the reaction was quenched using hydroquinone (1.0 g). The contents were cooled to room temperature and precipitated twice out of 10× (by weight) IPE/MeOH 95/5 (w/w). The polymer obtained was dried in vacuo after each precipitation step at 50° C. for 24 hours to yield 100 g polymer.

Example 23

Preparation and Processing of Photoresist Composition

A positive-tone photoresist composition was prepared by combining 21.088 g of a 10 wt % solution of the polymer from Example 20 in ethyl lactate, 18.979 g of a 2 wt % solution of the acid generator compound of Example 1 above in ethyl lactate, 1.898 g of a 0.5 wt % solution of 1,1',1'',1'''-(ethane-1,2-diylbis(azanetriyl))tetrapropan-2-ol in ethyl lactate, 0.422 g of a 0.5 wt % solution of fluorinated surfactant (Omnova PF656) in ethyl lactate, 47.342 g of ethyl lactate and 29.250 g of 2-hydroxyisobutyric acid methyl ester. The formulated resist was passed through a 0.01 μm PTFE filter. The thus prepared resist is spin coated onto a silicon wafer, soft baked to remove carrier solvent and exposed through a photomask to EUV radiation. The imaged resist layer is then baked at 110° C. for 60 seconds and then developed with an aqueous alkaline composition.

Example 24

Further Preparation and Processing of Photoresist Composition

A positive-tone photoresist composition was prepared by combining 24.038 g of a 10 wt % solution of the polymer from Example 19 in ethyl lactate, 40.865 g of a 2 wt % solution of the acid generator compound of Example 6 above in ethyl lactate, 5.288 g of a 0.5 wt % solution of 1,1',1'',1'''-(ethane-1,2-diylbis(azanetriyl))tetrapropan-2-ol in ethyl lactate, 0.481 g of a 0.5 wt % solution of fluorinated surfactant (Omnova PF656) in ethyl lactate, 21.302 g of ethyl lactate and 38.025 g of 2-hydroxyisobutyric acid methyl ester. The formulated resist was passed through a 0.01 μm PTFE filter. The thus prepared resist is spin coated onto a silicon wafer, soft baked to remove carrier solvent and exposed through a photomask to EUV radiation. The imaged resist layer is then baked at 110° C. for 60 seconds and then developed with an aqueous alkaline composition.

Example 25

Further Preparation and Processing of Photoresist Composition

A positive-tone photoresist composition was prepared by combining 6.997 g of a 10 wt % solution of the polymer from Example 19 in ethyl lactate, 11.889 g of a 2 wt % solution of the acid generator compound of Example 6 above in ethyl lactate, 9.232 g of a 0.5 wt % solution of 1,1',1''-nitrilotripropan-2-ol in ethyl lactate, 0.140 g of a 0.5 wt % solution of fluorinated surfactant (Omnova PF656) in ethyl lactate, 0.040 g of ethyl lactate and 11.705 g of 2-hydroxyisobutyric acid methyl ester. The formulated resist was passed through a 0.01 μm PTFE filter. The thus prepared resist is spin coated onto a silicon wafer, soft baked to remove carrier solvent and exposed through a photomask to EUV radiation. The imaged resist layer is then baked at 110° C. for 60 seconds and then developed with an aqueous alkaline composition.

Example 26

Further Preparation and Processing of Photoresist Composition

A positive-tone photoresist composition was prepared by combining 4.757 g of a 10 wt % solution of the polymer from Example 19 in ethyl lactate, 10.021 g of a 2 wt % solution of the acid generator compound of Example 7 above in ethyl lactate, 6.279 g of a 0.5 wt % solution of 1,1',1''-nitrilotripropan-2-ol in ethyl lactate, 0.095 g of a 0.5 wt % solution of fluorinated surfactant (Omnova PF656) in ethyl lactate, 0.060 g of ethyl lactate and 8.788 g of 2-hydroxyisobutyric acid methyl ester. The formulated resist was passed through a 0.01 μm PTFE filter. The thus prepared resist is spin coated onto a silicon wafer, soft baked to remove carrier solvent and exposed through a photomask to EUV radiation. The imaged resist layer is then baked at 110° C. for 60 seconds and then developed with an aqueous alkaline composition.

Example 27

Further Preparation and Processing of Photoresist Composition

A positive-tone photoresist composition was prepared by combining 8.012 g of a 10 wt % solution of the polymer from Example 19 in ethyl lactate, 9.690 g of a 2 wt % solution of the acid generator compound of Example 11 above in ethyl lactate, 0.833 g of a 0.5 wt % solution of 1,1',1'',1'''-(ethane-1,2-diylbis(azanetriyl))tetrapropan-2-ol in ethyl lactate, 0.160 g of a 0.5 wt % solution of fluorinated surfactant (Omnova PF656) in ethyl lactate, 9.604 g of ethyl lactate and 11.700 g of 2-hydroxyisobutyric acid methyl ester. The formulated resist was passed through a 0.01 μm PTFE filter. The thus prepared resist is spin coated onto a silicon wafer, soft baked to remove carrier solvent and exposed through a photomask to EUV radiation. The imaged resist layer is then baked at 110° C. for 60 seconds and then developed with an aqueous alkaline composition.

Example 28

Further Preparation and Processing of Photoresist Composition

A positive-tone photoresist composition was prepared by combining 4.815 g of a 10 wt % solution of the polymer from Example 21 in ethyl lactate, 13.002 g of a 2 wt % solution of the acid generator compound of Example 11 above in ethyl lactate, 1.589 g of a 0.5 wt % solution of 1,1',1'',1'''-(ethane-1,2-diylbis(azanetriyl))tetrapropan-2-ol in ethyl lactate, 0.096 g of a 0.5 wt % solution of fluorinated surfactant (Omnova PF656) in ethyl lactate, 1.723 g of ethyl lactate and 8.775 g of 2-hydroxyisobutyric acid methyl ester.

The formulated resist was passed through a 0.01 μm PTFE filter. The thus prepared resist is spin coated onto a silicon wafer, soft baked to remove carrier solvent and exposed through a photomask to EUV radiation. The imaged resist layer is then baked at 110° C. for 60 seconds and then developed with an aqueous alkaline composition.

Example 29

Further Preparation and Processing of Photoresist Composition

A positive-tone photoresist composition was prepared by combining 5.198 g of a 10 wt % solution of the polymer from Example 19 in ethyl lactate, 11.173 g of a 2 wt % solution of the acid generator compound of Example 17 above in ethyl lactate, 1.247 g of a 0.5 wt % solution of 1,1',1'',1'''-(ethane-1,2-diylbis(azanetriyl))tetrapropan-2-ol in ethyl lactate, 0.104 g of a 0.5 wt % solution of fluorinated surfactant (Omnova PF656) in ethyl lactate, 3.503 g of ethyl lactate and 8.775 g of 2-hydroxyisobutyric acid methyl ester. The formulated resist was passed through a 0.01 μm PTFE filter. The thus prepared resist is spin coated onto a silicon wafer, soft baked to remove carrier solvent and exposed through a photomask to EUV radiation. The imaged resist layer is then baked at 110° C. for 60 seconds and then developed with an aqueous alkaline composition.

Example 30

Further Preparation and Processing of Photoresist Composition

A positive-tone photoresist composition was prepared by combining 4.938 g of a 10 wt % solution of the polymer from Example 19 in ethyl lactate, 0.148 g of a 0.5 wt % solution of 1,1',1'',1'''-(ethane-1,2-diylbis(azanetriyl))tetrapropan-2-ol in ethyl lactate, 0.099 g of a 0.5 wt % solution of fluorinated surfactant (Omnova PF656) in ethyl lactate, 15.964 g of ethyl lactate and 8.852 g of 2-hydroxyisobutyric acid methyl ester. The formulated resist was passed through a 0.01 μm PTFE filter. The thus prepared resist is spin coated onto a silicon wafer, soft baked to remove carrier solvent and exposed through a photomask to EUV radiation. The imaged resist layer is then baked at 110° C. for 60 seconds and then developed with an aqueous alkaline composition.

Example 31

Further Preparation and Processing of Photoresist Composition

A positive-tone photoresist composition was prepared by combining 19.979 g of a 10 wt % solution of the polymer from Example 22 in ethyl lactate, 42.755 g of a 2 wt % solution of the acid generator compound of Example 6 above in ethyl lactate, 3.996 g of a 0.5 wt % solution of 1,1',1'',1'''-(ethane-1,2-diylbis(azanetriyl))tetrapropan-2-ol in ethyl lactate, 0.400 g of a 0.5 wt % solution of fluorinated surfactant (Omnova PF656) in ethyl lactate, 21.233 g of ethyl lactate and 36.638 g of 2-hydroxyisobutyric acid methyl ester. The formulated resist was passed through a 0.01 μm PTFE filter. The thus prepared resist is spin coated onto a silicon wafer, soft baked to remove carrier solvent and exposed through a photomask to EUV radiation. The imaged resist layer is then baked at 110° C. for 60 seconds and then developed with an aqueous alkaline composition.

Example 32

LWR Analyses

Developed relief images of photoresist compositions as set forth above were evaluated for linewidth roughness (LWR) with results provided in Table 1 below. LWR values were determined by top-down scanning electron microscopy (SEM) using a Hitachi 9380 CD-SEM, operating at an accelerating voltage of 800 volts (V), probe current of 8.0 picoamperes (pA), using 200 Kx magnification at 1.0 digital zoom, with the number of frames set to 64. LWR was measured over a 2 μm line length in steps of 40 nm, and reported as the average LWR for the measured region.

TABLE 1

| Photoresist composition of Example # | LWR (nm) |
|---|---|
| Example 23 (comparative) | 5.8 |
| Example 24 | 3.4 |
| Example 25 | 5.3 |
| Example 26 | 4.2 |
| Example 27 | 4.2 |
| Example 28 | 4.7 |
| Example 29 | 5.2 |
| Example 30 | 5.7 |
| Example 31 | 4.5 |

What is claimed is:
1. A method for providing a photoresist relief image, comprising:
 a) applying a coating layer of a photoresist composition on a substrate, the photoresist composition comprising:
  (a) a polymer; and
  (b) an acid generator selected from the group consisting of:
   (i) 5-(4-(2-(1-ethylcyclopentyloxy)-2-oxoethoxy)-3,5-dimethylphenyl)-5H-dibenzo[b,d]thiophenium 3-hydroxyadamantane-acetoxy-1,1,2,2-tetrafluorobutane-1-sulfonate;
   (ii) 5-(3,5-dimethyl-4-(2-oxo-2-(2-phenylpropan-2-yloxy)ethoxy)phenyl)-5H-dibenzo[b,d]thiophenium 3-hydroxyadamantane-acetoxy-1,1,2,2-tetrafluorobutane-1-sulfonate;
   (iii) 5-(4-(2-(1-ethylcyclopentyl oxy)-2-oxoethoxy)-3,5-dimethylphenyl)-5H-dibenzo[b,d]thiophenium 4-((4R)-4-((8R,9S,10S,13R,14S,17R)-10,13-dimethyl-3,7,12-trioxohexadecahydro-1H-cyclopenta[a]phenanthren-17-yl)pentanoyloxy)-1,1,2,2-tetrafluorobutane-1-sulfonate; and
   (iv) 5-(3,5-dimethyl-4-(2-oxo-2-(2-phenylpropan-2-yloxy)ethoxy)phenyl)-5H-dibenzo[b,d]thiophenium 44(4R)-44(8R,9S,10S,13R,14S,17R)-10,13-dimethyl-3,7,12-trioxohexadecahydro-1H-cyclopenta[a]phenanthren-17-ylipentanoyloxy)-1, 1,2,2-tetrafluorobutane-1-sulfonate; and
 b) exposing the photoresist composition layer to activating radiation and developing the exposed photoresist composition coating layer.
2. The method of claim 1 wherein the photoresist composition layer is exposed to EUV radiation.
3. The method of claim 1 wherein the photoresist composition layer is exposed to e beam radiation.
4. An acid generator that comprises a cation component selected from:

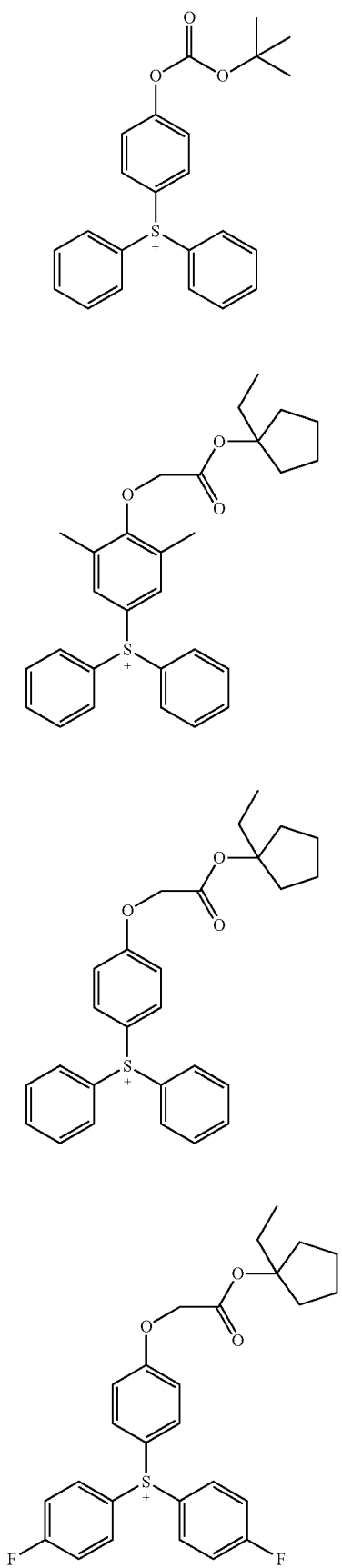

45
-continued
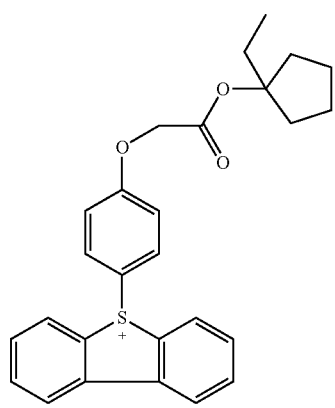
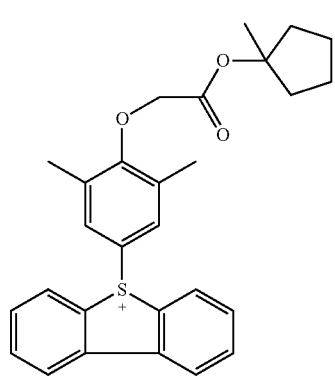
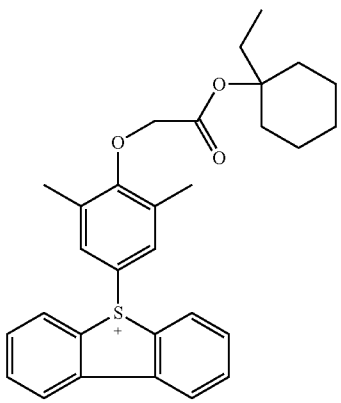
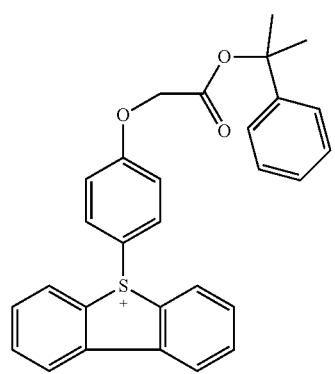
46
-continued
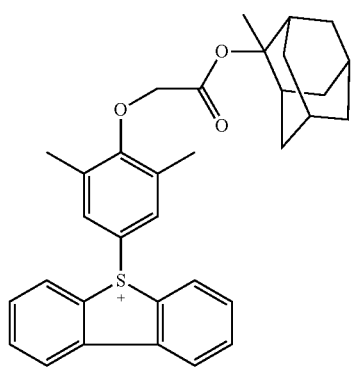
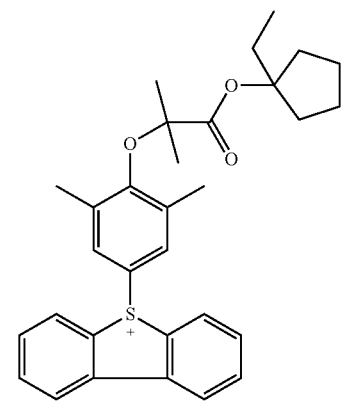
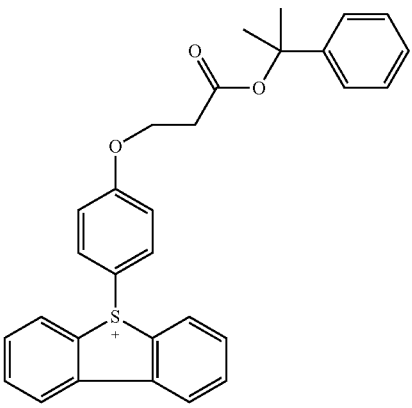
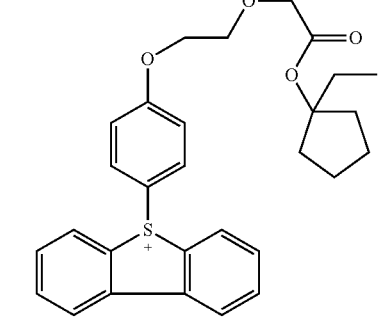

47
-continued
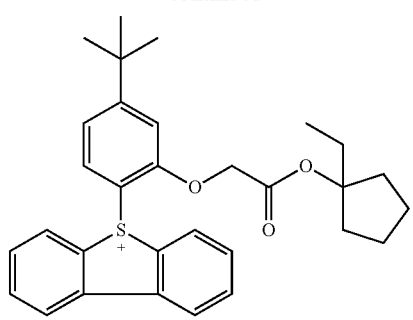
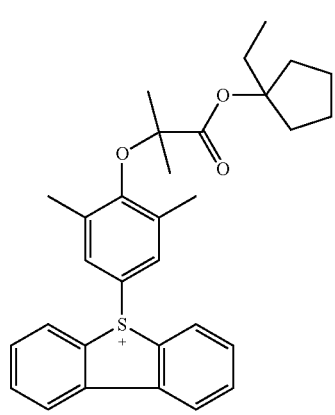
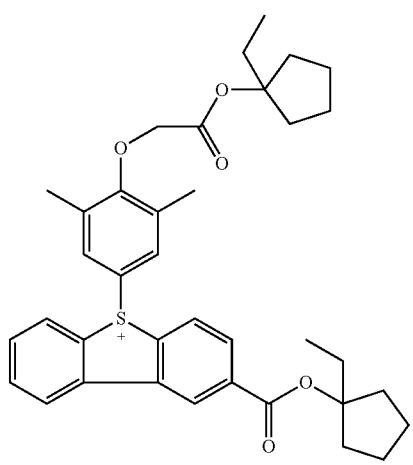
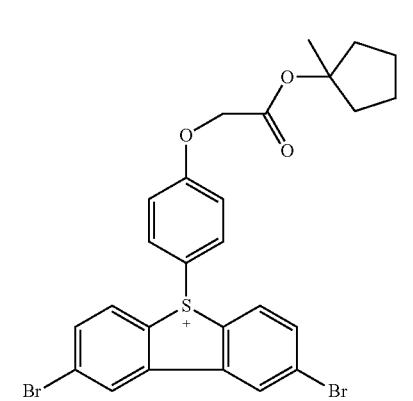
48
-continued
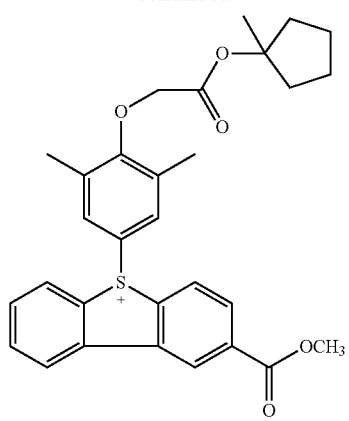
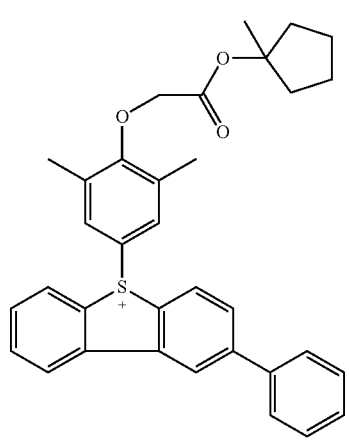
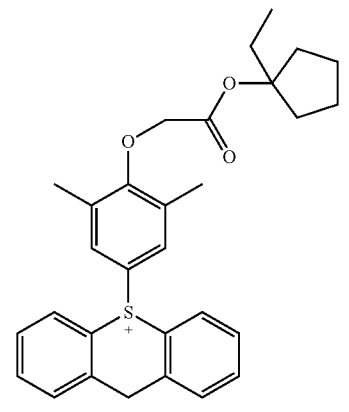
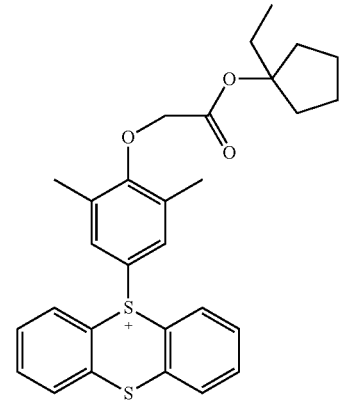

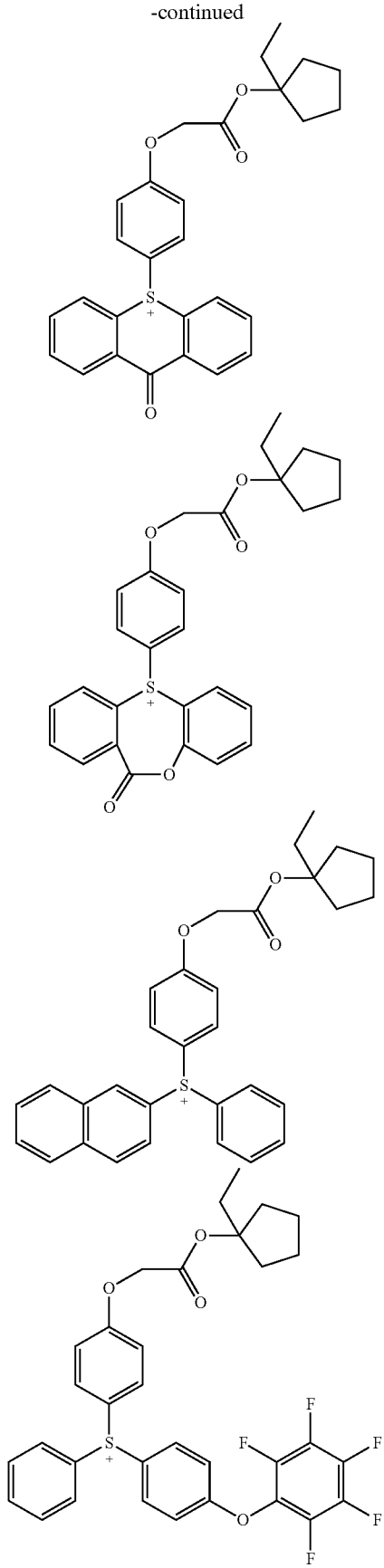

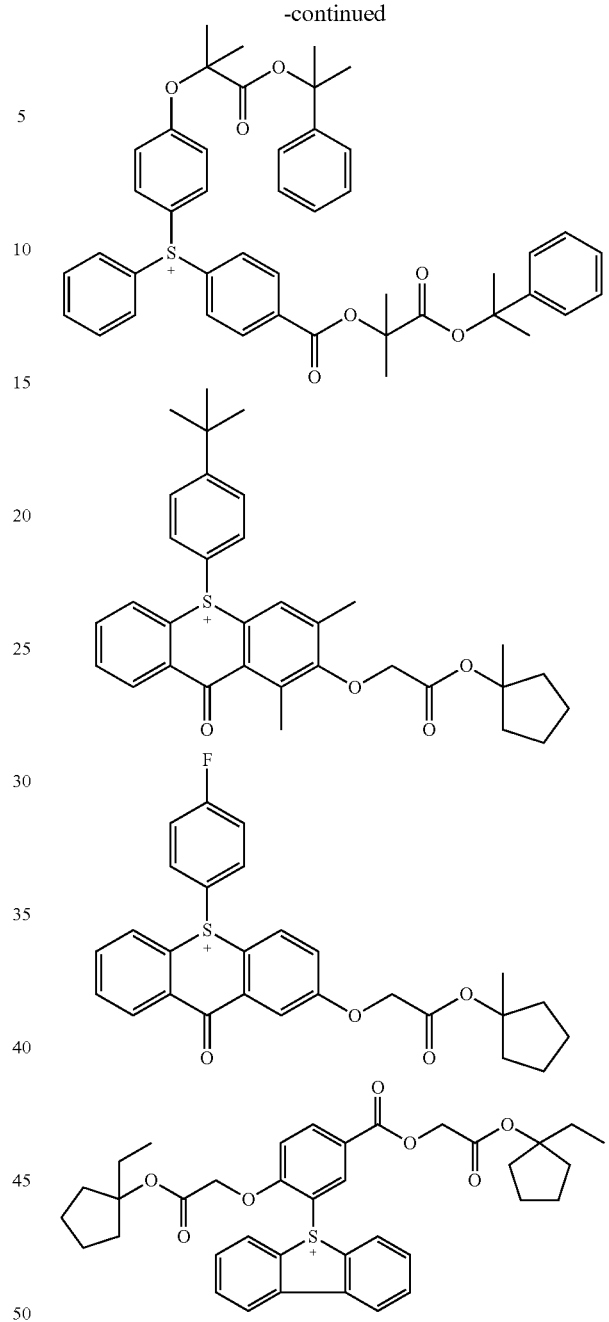

5. A photoresist composition comprising:
(a) a polymer; and
(b) an acid generator of claim 4.

6. A method for providing a photoresist relief image, comprising:
  a) applying a coating layer of a photoresist composition of claim 5 on a substrate; and
  b) exposing the photoresist composition layer to activating radiation and developing the exposed photoresist composition coating layer.

7. The method of claim 6 wherein the photoresist composition layer is exposed to EUV radiation.

8. The method of claim 6 wherein the photoresist composition layer is exposed to e beam radiation.

* * * * *